United States Patent [19]
Caskey et al.

[11] Patent Number: 5,582,989
[45] Date of Patent: Dec. 10, 1996

[54] MULTIPLEX GENOMIC DNA AMPLIFICATION FOR DELETION DETECTION

[75] Inventors: Charles T. Caskey; Jeffrey S. Chamberlain; Richard A. L. Gibbs; Joel E. Ranier; Phi N. Nguyen, all of Houston, Tex.

[73] Assignee: Baylor College of Medicine, Houston, Tex.

[21] Appl. No.: 315,673

[22] Filed: Sep. 30, 1994

Related U.S. Application Data

[63] Continuation of Ser. No. 60,463, May 12, 1993, abandoned, which is a continuation of Ser. No. 770,742, Oct. 2, 1991, abandoned, and a continuation of Ser. No. 256,689, Oct. 12, 1988, abandoned.

[51] Int. Cl.$^6$ .............................. C12Q 1/68; C12P 19/34
[52] U.S. Cl. ..................... 435/6; 435/91.1; 435/91.2; 536/22.1; 536/23.1; 536/24.1; 536/24.3; 536/24.31; 536/24.32; 536/24.33; 935/77; 935/78; 935/88
[58] Field of Search .................... 435/6, 91.1, 91.2; 536/22.1, 23.1, 24.1, 24.3–24.33; 935/77, 78, 88

[56] References Cited

FOREIGN PATENT DOCUMENTS

| | | |
|---|---|---|
| 0237362 | 9/1987 | European Pat. Off. . |
| 0256630 | 2/1988 | European Pat. Off. . |
| 0364255 | 4/1990 | European Pat. Off. . |

OTHER PUBLICATIONS

Farzadegan, H., et al, Loss of Human Immunodeficiency Virus Type 1 (HIV–1) Antibodies with Evidence of Viral–Infection in Asymptomatic Homosexual Men: A Report from the Multicenter AIDS Cohort Study, Ann–Intern–Med. 108:6, Jun. 1988, pp. 785–790.

Laure, F., et al, Detection of HIV 1 DNA in Infants and Children by Means of the Polymerase Chain Reaction, Lancet 2 (8610) 1988, pp. 538–541.

Newton, C. R., et al, Diagnosis of Alpha–1 Antitrypsin Deficiency by Enzymatic Amplification of Human Genomic DNA and Direct Sequencing of Polymerase Chain Reaction Products, Nucleic Acids Res. 16 (17), 1988, pp. 8233–8243.

Kawasaki, E. S., et al, Diagnosis of Chronic Myeloid and Acute Lymphocytic Leukemias by Detection of Leukemia–Specific Messenger RNA Sequences Amplified in–Intro, Proc. Natl Acad Sci U S A 85 (15), 1988, pp. 5698–5702.

Li, H., et al Amplification and Analysis of DNA Sequences in Single Human Sperm and Diploid Cells, Nature (Lond) 335 (6189), 1988, pp. 414–417.

Duggan, et al, HTLV–I–Induced Lymphoma Mimicking Hodgkin's Disease. Diagnosis by Polymerase Chain Reaction Amplification of Specific HTLV–I Sequences in Tumor DNA, Blood 71 (4), 1988, pp. 1027–1032.

Murakawa, G. J., et al, Direct Detection of HIV–1 RNA from AIDS and ARC Patient Samples, DNA (N Y) 7 (4), 1988, pp. 287–295.

(List continued on next page.)

*Primary Examiner*—W. Gary Jones
*Assistant Examiner*—Ardin H. Marschel
*Attorney, Agent, or Firm*—Fulbright & Jaworski LLP

[57] ABSTRACT

The present invention relates to a method for detecting multiple DNA sequences simultaneously. The method involves amplification of multiple sequences simultaneously by annealing a plurality of paired oligonucleotide primers to single stranded DNA. One member of each pair is complementary to the sense strand of a sequences and the other member is complementary to a different segment of the anti-sense strand of the same sequence. The amplification occurs by alternately annealing and extending the primers. The invention also includes oligonucleotide primer sequences helpful in detecting genetic diseases and/or exogenous DNA sequences.

15 Claims, 6 Drawing Sheets

OTHER PUBLICATIONS

Byrne, B. C., et al, Detection of HIV–1 RNA Sequences by In–Vitro DNA Amplification, Nucleic Acids Res. 16 (9), 1988, p. 4165.

Cai, S. P., et al, A Simple Approach to Prenatal Diagnosis of Beta Thalassemia in a Geographic Area where Multiple Mutations Occur, Blood 71 (5), 1988, pp. 1357–1360.

Dilella, A. G., et al, Screening for Phenylketonuria Mutations by DNA Amplification With the Polymerase Chain Reaction, Lancet 1 (8584), 1988, pp. 497–499.

Higuchi, R., et al, DNA Typing from Single Hairs, Nature (Lond) 332 (6164), 1988, pp. 543–546.

Ou, C–Y., et al, DNA Amplification for Direct Detection of HIV–1 in DNA of Peripheral Blood Mononuclear Cells, Science (Wash D C) 239 (4837), 1988, pp. 295–297.

Saiki, R. K., et al, Primer–Directed Enzymatic Amplification of DNA with Thermostable DNA Polymerase, Science (Wash D C) 239 (4839), 1988, pp. 487–491.

Scharf, S. J., et al, Direct Cloning and Sequence Analysis of Enzymatically Amplified Genomic Sequences, Science (Wash D C) 233 (4768), 1986, pp. 1076–1078.

Impriam, C. C., et al, Analysis of DNA Extracted from Formalin–Fixed, Paraffin–Embedded Tissues by Enzymatic Amplification and Hybridization with Sequence–Specific Oligonucleotides, Biochem Biophys Res Commun 142 (3), 1987, pp. 710–716.

Erlich, H. A., et al, Genetic Analysis Using Enzymatic Amplification of Specific Genomic Sequences, Current Communications in Molecular Biology: DNA Probes: Applications in Genetic and Infectious Disease and Cancer, Conference, Cold Spring Harbor Apr. 20–23, 1986, Illus Paper ISBN 0–87969–196–4, 1986, pp. 107–112.

Wong, C., et al, Characterization of Beta–Thalassemia Mutations Using Direct Genomic Sequences of Amplified Single Copy DNA, Nature (Lond) 330 (6146), 1987, pp. 384–386.

Mullis, K., et al, Specific Enzymatic Amplification of DNA In–Vitro: The Polymerase Chain Reaction, Dold Spring Harbor Laboratory, vol. 51, (parts 1 and 2), Molecular Biology of Homo Sapiens, Jun. 1986, XXV+702P, (Part 1), pp. 263–273.

Saiki, R. K., et al, Analysis of Enzymatically Amplified B–globin and HLA–DQa–DNA with Allele–Specific Oligonucleotide Probes, Nature (London) 324, 1986, pp. 163–166.

Kogan, S. C., An Improved Method for Prenatal Diagnosis of Genetic Diseases by Analysis of Amplified DNA Sequences, N. Engl. J. Med. 317, 1987, pp. 985–990.

Saiki, R. K., et al, Diagnosis of Sickle Cell Anemia and B Thalasemia with Enzymatically Amplified DNA and Non--Radioactive Allele–Specific Oligonucleotide Probes, N. Engl. J. Med. 319, 1988, pp. 537–541.

Chelly, J., et al, Transcription of the Dystrophin Gene in Muscle and Non–muscle Tissues, Nature (London) 333, 1988, pp. 858–860.

Darras, B. T., et al, Direct Method for Prenatal Diagnosis and Carrier Detection in Duchenne/Becker Muscular Dystrophy Using the Entire Dystrophin cDNA, Am. J. Med. Genet. 29, 1988, pp. 713–726.

Hejtmancik, J. F., et al, Carrier Diagnosis of Duchenne Muscular Dystrophy Using Restriction Fragment Length Polymorphisms, Neurology 36, 1986, pp. 1553–1562.

Kunkel, L. M., Analysis of Deletions in DNA From Patients with Becker and Duchenne Muscular Dystrophy, Nature (London) 322, 1986, pp.73–77.

Heiling, R., et al, A 230kb Cosmid Walk in the Duchenne Muscular Dystrophy Gene: Detection of a Conserved Sequence and of a Possible Deletion Prone Region, Nucl. Acids Res 15 (22), 1987, pp. 9129–9142.

Koenig, M., et al, Complete Cloning of the Duchenne Muscular Dystrophy (DMD) cDNA and Preliminary Genomic Organization of the DMD Gene in Normal and Affected Individuals, Cell 50, 1987, pp. 507–517.

Koenig, M., et al, The Complete Sequence of Dystrophin Predicts a Rod–Shaped Cytoskeletal Protein, Cell 53, 1988, pp. 219–288.

Chamberlain, J. S., et al, Expression of the Murine Duchenne Muscular Dystrophy Gene in Muscle and Brain, Science 239, 1988, pp. 1416–1418.

Chamberlain, J. R., et al, Deletion Screening of the Duchenne Muscular Dystrophy Locus Via Multiplex DNA Amplification, Nucleic Acids Res. 16(23), 1988, pp. 11141–11156.

Jeffrey, A. J., et al, Amplification of Human Minisatellites by the Polymerase Chain Reaction: Towards DNA Fingerprinting of Single Cells, Nucleic Acids Res. 16(23), 1988, pp. 10953–10971.

Chehab, F. F., et al, Detection of Sickle Cell Anaemia and Thalassaemias, Nature 329: 293, 1987.

Chamberlain, J. S., et al, Expression of the Murine Duchenne Muscular Dystrophy Gene in the Muscle and Brain of Normal and Mutant MDX Mice, J. Cell. Biol. 12C:319, 1988.

Chamberlain, J. S., et al., "Rapid detection of deletions at the Duchenne muscular dystrophy locus via multiplex genomic DNA amplification" *American Journal of Human Genetics* 43 (3 sup) (1988) Abstract 0711.

Stoflet, E. S., et al., "Genomic Amplificaion with Transcript Sequencing" *Science* 239:491–494 (1988).

Chamberlain, J. S., et al, Analysis of Duchenne Muscular Dystrophy Gene Mutations in Mice and Humans, Cellualr and Molecular Biology of Muscle Development, vol. 93, (Stockdale, F. and Kedes, L., eds), New York, Alan R. Liss Press, 1989, pp. 951–962.

Chamberlain, J. S., et al, Rapid detection of deletions at the Duchenne muscular dystropy locus via multiplex genomic DNA amplification, Amer. Journal of Human Genetics, 1988, vol. 43, p. A178, (0711) 3.2.

Kogan et al. (1987) The New England Journal of Medicine, vol. 317 (16) pp. 985–990.

MULTIPLEX GENOMIC DNA AMPLIFICATION FOR DELETION DETECTION

This application is a continuation of application Ser. No. 08/060,463, filed May 12, 1993, which was a continuation of application Ser. No. 07/770,742, filed Oct. 2, 1991, now abandoned, which was a continuation of application Ser. No. 07/256,689, filed Oct. 12, 1988, all now abandoned.

FIELD OF THE INVENTION

This invention relates to the field of simultaneous detection of deletions in genomic DNA sequences by the process of amplification of multiple sequences within the hemizygous or homozygous genome. The nucleic acid sequences are amplified by the process of simultaneous multiple repetitive reactions. This method of deletion detection is useful in a variety of areas including screening for genetic disease, and animal husbandry. Multiplex DNA amplification is also applicable to the simultaneous analysis of multiple genomic sequences and is useful in forensic medicine, disease screening, and in the development of recombinant or transgenic organisms.

BACKGROUND

This invention is an improvement on currently established procedures for the detection of genetic diseases resulting from mutations and deletions in genomic DNA sequences. Prenatal diagnosis and carrier detection of many X-linked diseases are available via Southern analysis using full length cDNA clones. Unfortunately, there are several major limitations that prevent widespread and routine use of Southern analysis for diagnosis of genetic disease. In many of the X-linked diseases, the defective sequences are unknown and probes are unavailable. In other diseases, such as X-linked muscular dystrophy, there are multiple exons, at least 60, scattered over a large area of genomic DNA, approximately 2.4 million bases. The introns average 35 Kb in length. In the case of muscular dystrophy, at least 7–9 separate cDNA subclones are necessary for Southern blot analysis to resolve each exon-containing restriction fragment for hyplotype assignment or diagnosis of genomic alterations. Furthermore, Southern analysis is an expensive, tedious, and time-consuming technique that requires the use of radioisotopes, making it unsuitable for routine use in clinical laboratories.

An alternative to Southern analysis for mutation and deletion detection is the polymerase chain reaction (PCR) described by Mullis et al. in U.S. Pat. No. 4,683,195 which issued on Jul. 28, 1987 and by Mullis in U.S. Pat. No. 4,683,202 which issued on Jul. 28, 1987. With PCR, specific regions of a gene can be amplified up to a million-fold from nanogram quantities of genomic DNA. After amplification the nucleic acid sequences can be analyzed for the presence of mutant alleles either by direct DNA sequencing or by hybridization with allele-specific oligonucleotide probes. The PCR technique has proven useful in the diagnosis of several diseases including β-thalassemia, hemophilia A, sickle cell anemia and phenylketonuria. Routine screening for genetic diseases and exogenous DNA sequences, such as virus, with PCR, has been limited by the ability to conduct tests for only a single sequence at a time. Screening for a plurality of possible DNA sequences requires a cumbersomely large number of separate assays, thus increasing the time, expense, and tedium of performing such assays. For example, in some diseases, such as Duchenne muscular dystrophy (DMD), PCR diagnosis has been limited since point mutations leading to DMD have not been identified. Approximately 60% of the cases of DMD are due to deletions. The other 40% are unknown at present, but probably involve mutations of the intron-exon splice sites or the creation of premature stop codons. Thus a large gene like the DMD gene must be screened with multiple assays.

In both U.S. Pat. Nos. 4,683,195 and 4,683,202, procedures are described for amplification of specific sequences. Both patents describe procedures for detecting the presence or absence of at least one specific nucleic acid sequence in a sample containing a mixture of sequences. Although the patents claim at least one sequence and state that multiple sequences can be detected, they do not provide an effective procedure for amplifying multiple sequences at the same time. In the examples, single sequences are amplified or multiple sequences are amplified sequentially. Adding primers for a second sequence is usually possible, but when primers for more than two sequences are added the procedure falls apart. The present application is an improvement on the PCR method and solves the problems encountered when primers for multiple sequences are reacted simultaneously. The present invention describes a procedure for simultaneous amplification of multiple sequences, and for the application of this multiplex amplification procedure in order to detect a plurality of deletions within the same gene or within multiple genes.

The procedures of the present application provide improved methods for the detection of deletions in hemizygous genes on the X and Y chromosomes. The procedures are effective in detecting genetic diseases caused by deletions on the X or Y chromosome, for example, DMD. They are also effective in detecting homozyous deletions and may be used to simultaneously screen for many possible homozygous or hemizygous deletions as long as parts of the appropriate genetic sequences are known. The procedure for multiplex amplification also enables simultaneous analysis of multiple genetic loci regardless of the presence or absence of deletions.

SUMMARY OF THE INVENTION

An object of the present invention is a method for simultaneously detecting deletions at a plurality of genomic DNA sequences.

An additional object of the present invention is to detect X-linked genetic diseases.

A further object of the present invention is the diagnosis of DMD.

A further object of the present invention is to simultaneously analyze multiple genetic loci for polymorphisms and/or non-deletion mutations.

Thus, in accomplishing the foregoing objects there is provided in accordance with one aspect of the present invention, a method for simultaneously detecting deletions at a plurality of genomic DNA sequences, comprising the steps of:

Treating said genomic DNA to form single stranded complementary strands;

Adding a plurality of paired oligonucleotide primers, each pair specific for a different sequence, one primer of each pair substantially complementary to a part of the sequence in the sense strand and the other primer of each pair substantially complementary to a different part of the same sequence in the complementary anti-sense strand;

Annealing the plurality of primers to their complementary sequences;

Simultaneously extending said plurality of annealed primers from each primer's 3' terminus to synthesize an extension product complementary to the strands annealed to each primer, said extension products, after separating from their complement, serving as templates for the synthesis of an extension product from the other primer of each pair;

Separating said extension products from said templates to produce single-stranded molecules;

Amplifying said single stranded molecules by repeating at least once, said annealing, extending and separating steps; and Identifying said amplified extension products from each different sequence.

Additional embodiments include detection of deletions at a plurality of genomic DNA sequences on the X and Y chromosomes or on autosomal chromosomes when the deletions are homozygous. A variety of X-linked diseases can be detected including ornithine transcarbamylase deficiency, hypoxanthine phosphoribosyltransferfase deficiency, steroid sulfatase deficiency and X-linked muscular dystrophy.

In another embodiment, X-linked muscular dystrophy is detected using a plurality of paired primers which are complementary to different sequences within the gene coding for the protein dystrophin. Other embodiments include multiple oligonucleotide primers useful in detecting X-linked genetic disease.

Other and further objects, features and advantages will be apparent from the following description of the presently preferred embodiments of the invention given for the purpose of disclosure when taken in conjunction with the accompanying drawings.

BRIEF DESCRIPTION OF THE DRAWINGS

The invention will be more readily understood from a reading of the following specification and by references to the accompanying drawings, forming a part thereof.

Figure 1:
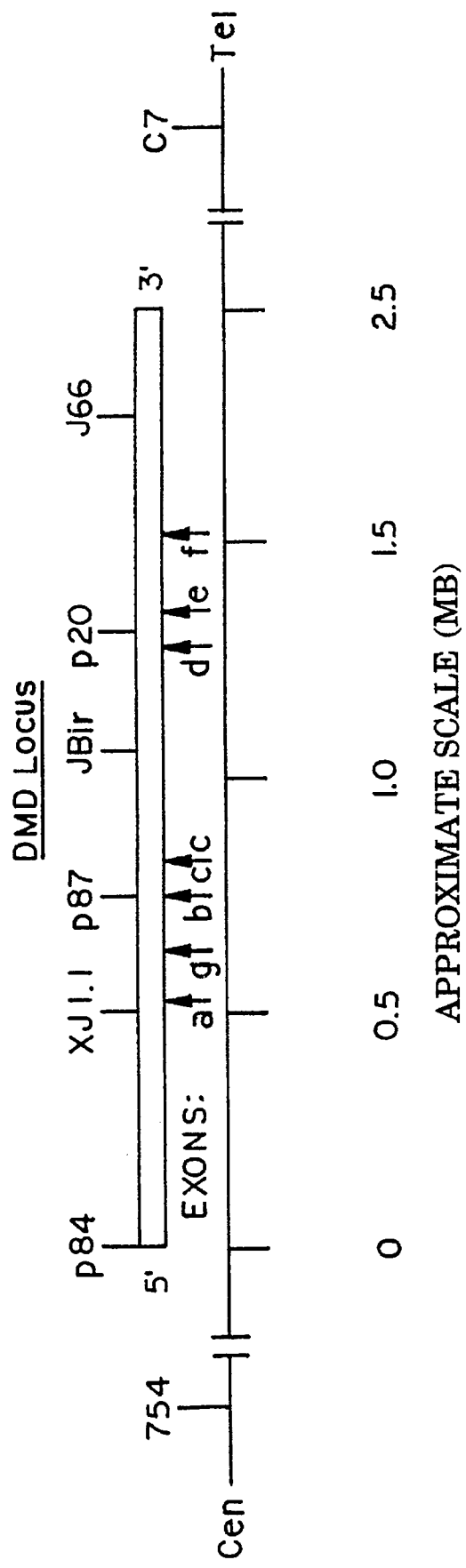
FIG. 1 is a schematic representation of the DMD gene illustrating the approximate size of the locus, the position of the amplified fragments and the location of the genomic regions that have been cloned and sequenced.

The drawings are not necessarily to scale and certain features of the invention may be exaggerated in scale or shown in schematic form in the interests of clarity and conciseness.

DETAILED DESCRIPTION

It will be readily apparent to one skilled in the art that various substitutions and modifications may be made to the invention disclosed herein, without departing from the scope and spirit of the invention.

The term "oligonucleotide primers" as used herein defines a molecule comprised of more than three deoxyribonucleotides or ribonucleotides. Its exact length will depend on many factors relating to the ultimate function and use of the oligonucleotide primer, including temperature, source of the primer and use of the method. The oligonucleotide primer can occur naturally, as in a purified restriction digest, or be produced synthetically. The oligonucleotide primer is capable of acting as an initiation point for synthesis when placed under conditions which induce synthesis of a primer extension product complementary to a nucleic acid strand. The conditions can include the presence of nucleotides and an inducing agent such as a DNA polymerase at a suitable temperature and pH. In the preferred embodiment, the primer is a single-stranded oligodeoxyribonucleotide of sufficient length to prime the synthesis of an extension product from a specific sequence in the presence of an inducing agent. In the deletion detection procedure, the oligonucleotides are usually at least greater than 12 mers in length. In the preferred embodiment, the oligonucleotide primers are about 18 to 29 mers in length. Sensitivity and specificity of the oligonucleotide primers are determined by the primer length and uniqueness of sequence within a given sample of template DNA. Primers which are too short, for example, less than about 12 mer may show non-specific binding to a wide variety of sequences in the genomic DNA and thus are not very helpful. In the preferred embodiment, the oligonucleotide primer is usually selected for its ability to anneal to intron sequences in the proximity of the 5' or 3' end of the exon or to anneal to a sequence at the intron-exon junction. Since the known deletion defects resulting in genetic diseases result from deletions that include the exons or intron-splice site regions, it is preferable to have primers complementary to intron sequences.

Each primer pair herein was selected to be substantially complementary to the different strands of each specific sequence to be amplified. Thus, one primer of each pair is sufficiently complementary to hybridize with a part of the sequence in the sense strand and the other primer of each pair is sufficiently complementary to hybridize with a different part of the same sequence in the anti-sense strand. Thus, although the primer sequence need not reflect the exact sequence of the template, the more closely it does reflect the exact sequence the better the binding during the annealing stage.

Within a primer pair, each primer preferably binds at a site on the sequence of interest distant from the other primer. In the preferred embodiment the distance between the primers should be sufficient to allow the synthesis of an extension product between the two binding sites, yet close enough so that the extension product of each primer, when separated from its template, can serve as a template for the other primer. The extension products from the two paired primers are complementary to each other and can serve as templates for further synthesis. The further apart the binding sites, the more genomic DNA there is which can be screened. However, if the distance is too great the extension products will not efficiently overlap with the primers and thus amplification will not occur.

As used herein the term "extension product" refers to the nucleotide sequence which is synthesized from the 3' end of the oligonucleotide primer and which is complementary to the strand to which the oligonucleotide primer is bound.

As used herein the term "differentially labeled" shall indicate that each extension product can be distinguished from all the others because it has a different label attached or is of a different size or binds to a specifically labelled oligonucleotide. One skilled in the art will recognize that a variety of labels are available. For example, these can include radioisotopes, fluorescers, chemiluminescers, enzymes and antibodies. Various factors affect the choice of the label. These include the effect of the label on the rate of hybridization and binding of the primer to the DNA, the sensitivity of the label, the ease of making the labeled primer, probe or extension products, the ability to automate, available instrumentation, convenience and the like. For example, a different radioisotope could be used such as $^{32}P$, $^{3}H$, or $^{14}C$; a different fluorescer such as fluorescein, tetramethylrhodamine, Texas Red or 4-chloro-7- nitrobenzo-2-oxa-1-diazole (NBD); or a mixture of different labels such as radioisotopes, fluorescers and chemiluminescers. Alternatively, the primers can be selected such that the amplified extension products for each sequence are of different lengths and thus can be separated by a variety of methods known in the art. Similarly, the extension products could include a restriction fragment length polymorphism which could be used to distinguish different extension products. In these examples, each primer or its extension product can be differentiated from all the other primers when they are in a mixture. Alternatively, probes which bind to the amplified extension products could be labeled and sets of probes which distinguish alleles of a single sequence within a multiplex DNA amplification reaction may be used whether or not labelled.

Each specific, different DNA sequence, which is to be detected herein, can derive from genomic DNA of the organism or exogenous DNA such as virus, bacteria or parasites. The source of genomic DNA from the organism to be tested can be blood, hair or tissue (including chorionic villi, amniotic cells, fibroblasts and biopsies). The source of DNA may be freshly obtained or have been suitably stored for extended periods of time. The DNA must be of sufficient quality to permit amplification. The genomic DNA can be prepared by a variety of techniques known to one skilled in the art.

As used herein, the term "deletion" refers to those genomic DNA sequences in which one or more nucleic acid base has been deleted from the sequence and thus is no longer present in the gene. The size of the deletion can affect the sensitivity of the amplification procedure. Generally, the larger the deletion the larger the sensitivity.

Any specific known nucleic acid sequence can be detected by the present method. Preferably, at least part of the sequence is deleted from the genome. It is only necessary that a sufficient number of bases at both ends of the sequence be known in sufficient detail to prepare oligonucleotide primers which will hybridize to the different strands of the desired sequence at relative positions along the sequence.

The oligonucleotide primers may be prepared using any suitable method, for example, phosphotriester and phosphodiester methods or automated embodiments thereof, the synthesis of oligonucleotides on a modified solid support, the isolation from a biological source (restriction endonuclease digestion), and the generation by enzymatically directed copying of a DNA or RNA template.

One embodiment of the present invention is a method for simultaneously detecting deletions at a plurality of DNA sequences, comprising the steps of: treating said DNA to form single stranded complementary strands; adding a plurality of paired oligonucleotide primers, each pair specific for a different sequence, one primer of each pair substantially complementary to a part of the sequence in the sense-strand and the other primer of each pair substantially complementary to a different part of the same sequence in the complementary anti-sense strand; annealing the plurality of primers to their complementary sequences; simultaneously extending said plurality of annealed primers from each primer's 3' terminus to synthesize an extension product complementary to the strands annealed to each primer, said extension products, after separation from the complement, serving as templates for the synthesis of an extension product from the other primer of each pair; separating said extension products from said templates to produce single-stranded molecules; amplifying said single-stranded molecules by repeating, at least once, said annealing, extending and separating steps; and identifying said amplified extension product from each different sequence.

One preferred embodiment of the present invention is a method for detecting deletions at a plurality of genomic DNA sequences, wherein said sequences are selected from a group of sequences on the X and Y chromosomes. It is preferrable to detect hemizygous genes on the X and Y chromosomes, since this increases the level of sensitivity. When the procedure is used to detect the heterozygous state, it requires quantitative measurement, and thus is much less efficient than detecting the presence or absence of sequences as is done for hemizygous genes. For example, if part of an exon has been deleted the multiplex amplification method of the present invention will detect this by either failing to produce an oligonucleotide sequence or by production of an oligonucleotide sequence of a different size. Furthermore multiple exons can be screened at the same time. Thus, it is easy to detect the presence of a deletion. However, in looking at heterozygous states, where the chromosomes have one normal gene and one deleted gene, the normal gene will produce a normal product, and thus there is the necessity to measure the quantitative difference in the production of extension products.

A second embodiment of the present invention is to permit simultaneous amplification of multiple, possibly unrelated sequences for the purpose of their simultaneous analysis. Such analysis may simply involve the determination of whether exogenous sequences (virus, bacteria or other parasites) are present within a sample of DNA, or might involve the detection of polymorphisms or mutations within a plurality of sequences. The polymorphisms or mutations can be detected by a variety of methods well known to those skilled in the art. The methods include, but are not limited to, direct DNA sequencing, allele-specific oligonucleotide hybridization, and competitive oligonucleotide priming.

The multiplex genomic DNA amplification method is preferably used to detect X-linked diseases resulting from deletions in the genomic DNA sequence. Genetic diseases can be caused by a variety of mechanisms including mutations and deletions. The procedure described herein was developed for detection of genetic diseases which result from deletions within the genome. Examples of some X-linked diseases which are candidates for the use of multiplex genomic DNA amplification are ornithine transcarbamylase deficiency, hypoxanthine phosphoribosyltransferase deficiency, steroid sulfatase deficiency and X-linked muscular dystrophy. Other disorders on the X chromosome or genes on the Y chromosome can also be easily detected. The procedure is also applicable to the detection of any set of known point mutations within a set of genomic sequences. The procedure is also applicable to the simultaneous detection of any set of exogenous DNA sequences in a given DNA sample. The procedure is also applicable to the simultaneous detection of any set of polymorphic or variable tandemly repetitive sequences within a genone.

The advantages of the multiplex amplification system are that numerous diseases or specific DNA sequence alterations can be detected in the same assay. For example, primers to hypoxanthine phosphoribosyltransferfase deficiency, steroid sulfatase deficiency, X-linked muscular dystrophy, ornithine transcarbamylase deficiency and other X-linked diseases can all be run simultaneously on the same sample. Furthermore, the multiplex amplification procedure is useful for very large genes with multiple exons, such as the dystrophin gene. Because of the large size of the dystrophin locus, Mullis type PCR amplification is not able to scan the whole gene in one assay. Thus, it is necessary for multiple site amplification within the gene to detect all possible deletions which could result in disease. Deletions at the DMD locus can encompass any of the approximately 60 plus exons which are distributed over more than 2 million bases of DNA. Virtually all of these exons are separated by large introns and so up to 60 separate reactions could be required for complete analysis of DMD deletions. To simplify this task, the present invention of a multiplex genomic DNA amplification for deletion detection can be employed to perform simultaneous examination of multiple exons. For example, oligonucleotide primers flanking separate DMD gene exons can be synthesized and combined and used for multiplex DNA applications. At present, up to at least 7 different DMD gene sequences have been examined simultaneously. The entire procedure for the multiplex amplification from start-up to photography of the results takes less than 5 hours. The relative locations of the amplified regions do not affect the results and exons have been amplified which have been separated by at least 1000 kb. The PCR amplification technique of Mullis is adequate for one and possibly two pair of primers, but when greater than two pairs of primers are used the procedure will not adequately amplify all the appropriate sequences.

One skilled in the art readily appreciates that as more exon gene sequences become available the applicability of this test will expand to examine for deletions in multiple genes at the same time or examine multiple sites within the same gene at the same time. The later example is important for genes such as dystrophin which are so large that primers annealed to the ends of the gene will not traverse the whole gene sequence. Thus the necessity of doing multiple analysis to detect deletions in different regions of the gene. In addition, as specific mutations within multiple unrelated genes become known, multiplex DNA amplification can be applied to simultaneously assay for the presence of any of these mutations.

Furthermore, as specific or highly variable DNA sequence polymorphisms become known in various genetic Loci, multiplex DNA amplification can be used to simultaneously analyze these polymorphisms to determine the haplotype or to determine the identity or source of DNA (genetic footprinting).

The number of analyses which can be run simultaneously is unlimited, however, the upper limit is probably about 20 and is dependent on the size differences required for resolution and/or the number of labels or methods which are available to resolve the extension products. The ability to simultaneously amplify only 9 exons would allow the detection of greater than 90% of all known DMD deletions in a single reaction. The ability to simultaneously amplify even as few as 10 exons allows the rapid and simple diagnosis of DMD deletions using only a few separate reactions. Assuming that there are about 60 exons in the DMD gene and that the exons are widely separated such that primers are needed for every exon, a maximum of 6 separate assays is needed to detect all deletions in this gene. Under the same assumptions the Mullis PCR method would require 60 separate reactions to detect the deletions in this gene. Thus, as the size of the gene increases and the number of exons which cannot be detected together increases the advantages of this method are greatly enhanced. Furthermore, use of an automatic PCR apparatus (such as that produced by Perkin-Elmer/Cetus) and DNA sequencing machines will facilitate resolution and detection of amplified DNA fragments, will help automate the assay and will lead to the method being applied routinely in clinical laboratories without the need for highly trained research personnel.

The following examples are offered by way of illustration and are not intended to limit the invention in any manner. In the examples all percentages are by weight, if for solids and by volume if for liquids, and all temperatures are in degrees Celsius unless otherwise noted.

EXAMPLE 1

The following conditions are currently in use to perform simultaneous amplification of a plurality of separate genomic regions within the human DMD gene. These conditions may need to be slightly modified depending on the particular regions to be amplified, the number and length of sequences to be amplified, and the choice of oligonucleotide primers. The time of reaction is highly dependent on the overall sequence length. Thus, as the number of amplified sequences increase and/or the length of amplified sequences increases, the time must be increased. The temperature is dependent on the length, the uniqueness of the primer sequence and the relative percentage of GC bases. The longer the primers, the higher the temperature needed. The more unique the sequence, the lower the temperature needed to amplify. GC rich primers need higher temperatures to prevent cross hybridization and to allow unique amplification. However, as the AT percentage increases, higher temperatures cause these primers to melt. Thus, these primers must be lengthened for the reaction to work.

Template DNA was prepared from the tissue chosen for analysis using a variety of well-established methods known to those skilled in the art. Typically, 100 µl reaction volumes were utilized. Approximately 500 ng of DNA was added to a solution comprised of the following: 67 mM Tris-HCL [pH 8.8 at 25°]; 6.7 mM magnesium chloride; 16.6 mM ammonium sulfate; 10 mM β-mercaptoethanol; 6.7 μM ethylene diamine tetra-acetic acid (EDTA); and 170 μg/mL bovine serum albumin. This solution can be prepared beforehand and appears to be stable for very long periods of storage at −70°. The enzyme, Taq polymerase, was added to achieve a final concentration of 100 units/mL. This reaction mixture was gently mixed. The reaction mixture was overlaid with about 50 μL of paraffin oil, and the reaction vessel (preferably a 0.5 ml microcentrifuge tube) was centrifuged at 14,000×g for 10 sec. Amplification was performed either by manually transferring the reaction vessels between glycerol filled heat blocks at the appropriate temperatures, or automatically transferring the reaction vessels with a Perkin-Elmer/Cetus thermocycler using the 'step-cycle' functions. The reaction was controlled by regulated and repetitive temperature changes of various duration. Initially the reaction was heated to 94° for 7 minutes. Subsequently 25 cycles of the following temperature durations were applied: 94° for 1 minute, then 55° for 45 seconds, then 65° for 3½ minutes. Following completion of the final cycle the reaction was incubated at 65° for an additional 7 minutes. Reactions were then stored at 4° until analysis.

Genomic DNA deletions and/or exogenous DNA sequences were determined by examining the amplification products. For example, the lack of an expected amplification product indicates a deletion. Many methods for this determination are known to those skilled in the art. The preferred method involves electrophoresis of about one-twentieth of the reaction on a 1.4% (weight/vol) agarose gel in the following buffer: 40 mM tris-HCl; 20 mM sodium acetate, 1 mM EDTA (adjusted to pH 7.2 with glacial acetic acid), and 0.5 μg/μl. of ethidium bromide. Electrophoresis was performed at 3.7 volts/cM for 100 minutes per 14 cM of agarose gel length. Analysis was completed by examining the electrophoresed reaction products on an ultraviolet radiation transilluminator, and the results were photographed for permanent records.

When the analysis requires determination of DNA sequence polymorphisms or mutations within individual amplification products the agarose gel is transferred to an appropriate DNA binding medium such as nitrocellulose using well-established procedures, for example, Southern blotting. Individual DNA sequences within the amplified DNA fragments can be determined by a variety of techniques including allele-specific oligonucleotide hybridization. Alternatively, reaction products may be further analyzed prior to electrophoresis on agarose gel by competitive oligonucleotide primer amplification, using separate allele-specific primers for each amplified DNA sequence of the multiplex amplification reaction products.

A third method for determining DNA sequence differences within individual amplification products does not require electrophoresis. In this method, aliquots of the multiplex amplification reaction are sequentially applied to an appropriate DNA binding membrane such as nitrocellulose, and then each aliquot is analyzed via hybridization with individual members of sets of allele-specific oligonucleotide (ASO) probes, each separate aliquot being hybridized with one member of a pair of ASO probes specific for one member of the multiply amplified DNA sequences.

EXAMPLE 2

FIG. 1 is a schematic representation of the DMD locus. The relative location of the exons used in the DMD gene amplification examples are illustrated.

For detection of DMD, a variety of probes can be used either in individual PCR reactions or in combinations in multiplex PCR reactions. These probes are shown in Table 1.

TABLE 1

Summary of DMD gene multiplex amplification primer sets.

| | Exon and Size | Primer Sequence | Amplified | Deleted | Tm* °C. |
|---|---|---|---|---|---|
| a. | Exon 8 (182 bp) | F-GTCCTTTACACACTTTACCTGTTGAG R-GGCCTCATTCTCATGTTCTAATTAG | 360 bp | 11.3% | 73.0 73.0 |
| b. | Exon 17 (178 bp) | F-GACTTTCGATGTTGAGATTACTTTCCC R-AAGCTTGAGATGCTCTCACCTTTTCC | 416 bp | 9.4% | 77.4 79.9 |
| c. | Exon 19 (88 bp) | F-TTCTACCACATCCCATTTTCTTCCA R-GATGGCAAAAGTGTTGAGAAAAAGTC | 459 bp | 10.3% | 78.1 77.0 |
| d. | 4.1 Kb Hind III (148 bp) | F-CTTGATCCATATGCTTTTACCTGCA R-TCCATCACCCTTCAGAACCTGATCT | 268 bp | 4.0% | 76.9 79.3 |
| e. | 0.5 Kb Hind III (176 bp) | F-AAACATGGAACATCCTTGTGGGGAC R-CATTCCTATTAGATCTGTCGCCCTAC | 547 bp | 8.4% | 81.3 76.3 |
| f. | 1.2/3.8 Kb Hind III (159 bp) | F-TTGAATACATTGGTTAAATCCCAACATG R-CCTGAATAAAGTCTTCCTTACCACAC | 506 bp | 18.2% | 78.8 74.3 |
| g. | Exon 12 (151 bp) | F-GATAGTGGGCTTTACTTACATCCTTC R-GAAAGCACGCAACATAAGATACACCT | 337 bp | 9.6% | 73.7 77.4 |
| | | | Total: | 38% | |

*Tm = melting temperature, i.e., that temperature at which 50% of strands are dissociated at 1M monovalent cation concentration, calculated by the nearest neighbor method.

In Table 1 each exon is designated a, b, c, d, e, f, or g and corresponds to the same letter in FIG. 1. When the exon number is known it is listed. If the exon number is not known, the size of the genomic Hind III fragment containing that exon is listed. Also shown is the size of the exon in base pairs (bp). The PCR primer sequences are shown in 5'—3' orientation. The forward primer (F), hybridizes 5' of the exon, and the reverse primer (R), hybridizes 3' of the exon. The size of the amplified fragment obtained with each primer set is also shown.

The percentage of analyzed DMD patients that are deleted for each indicated exon is shown in column four. This total number is less than the sum of the individual exon deletion frequencies because many deletions encompass multiple exons.

In Table 2 are the exon and flanking intron sequences for Exon 17. The exon is from 227 to 402. The primer sequences used to amplify this sequence are 7 to 33 and 396 to 421.

TABLE 2

| 5' 10 | 20 | 30 | 40 | 50 |
|---|---|---|---|---|
| TAAATTGACT | TTCGATGTTG | AGATTACTTT | CCCTTGCTAT | TTCAGTGAAC |
| 60 | 70 | 80 | 90 | 100 |
| CAAACTTAAG | TCAGATAAAA | CAATTTTATT | TGGCTTCAAT | ATGGTGCTAT |
| 110 | 120 | 130 | 140 | 150 |
| TTTGATCTGA | AGGTCAATCT | ACCAACAAGC | AAGAACAGTT | TCTCATTATT |
| 160 | 170 | 180 | 190 | 200 |
| TTCCTTTGCC | ACTCCAAGCA | GTCTTTACTG | AAGTCTTTCG | AGCAATGTCT |
| 210 | 220 | 230 | 240 | 250 |
| GACCTCTGTT | TCAATACTTC | TCACAGATTT | CACAGGCTGT | CACCACCACT |
| 260 | 270 | 280 | 290 | 300 |
| CAGCCATCAC | TAACACAGAC | AACTGTAATG | GAAACAGTAA | CTACGGTGAC |
| 310 | 320 | 330 | 340 | 350 |
| CACAAGGGAA | CAGATCCTGG | TAAAGCATGC | TCAAGAGGAA | CTTCCACCAC |
| 360 | 370 | 380 | 390 | 400 |
| CACCTCCCCA | AAAGAAGAGG | CAGATTACTG | TGGATTCTGA | AATTAGGAAA |
| 410 | 420 | 430 | 440 | 450 |
| AGGTGAGAGC | ATCTCAAGCT | TTTATCTGCA | AATGAAGTGG | AGAAAACTCA |
| 460 | 470 | 480 | 490 | 500 |
| TTTACAGCAG | TTTTGTTGGT | GGTGTTTTCA | CTTCAGCAAT | ATTTCCAGAA |
| 510 | 520 | 530 | 540 | 550 |
| TCCTCGGGTA | CCTGTAATGT | CAGTTAATGT | AGTGAGAAAA | ATTATGAAGT |
| 560 | 570 | 580 | 590 | 600 |
| ACATTTTAAA | ACTTTCACAA | GAAATCACTA | TCGCAACAGA | AACTAAATGC |
| 610 | 620 | 630 | 640 | 650 |
| TTAATGGAAA | TGGTGTTTTC | TGGGGTGAAA | GAAGAAACTA | TAGAAACTAT |
| 660 | 670 | 680 | 690 | 700 |
| AGGTGATAAA | CTACTGTGGT | AGCATTTTAA | TCCTAAAAGT | TTCTTTCTTT |
| 710 | 720 | 730 | 740 | 750 |
| CTTTTTTTTT | TTTCTTCCTT | ATAAAGGGCC | TGCTTGTTGA | GTCCCTAGTT |
| 760 | 770 | 780 | 790 | 800 |
| TTGCATTAAA | TGTCTTTTTT | TTCCAGTAAC | GGAAAGTGCA | TTTTCATGAA |
| 810 | 820 | 830 | 840 | 850 |
| GAAGTACACC | TATAATAGAT | GGGATCCATC | CTGGTAGTTT | ACGAGAACAT |
| 860 | 870 | 880 | 890 | 900 |
| GATGTCTCAG | TCTGCGCATC | CTAAATCAGG | AGTAATTACA | GAACACATTT |
| 910 | 920 | 930 | 940 | 950 |
| CCTGTTCTTT | GATATTTATA | AAGTCTTATC | TTGAAGGTGT | TAGAATTTTT |
| 960 | 970 | 980 | 990 | 1000 |
| AACTGATCTT | TTTGTGACTA | TTCAGAATTA | TGCATTTTAG | ATAAGATTAG |
| 1010 | 1020 | 1030 | 1040 | |
| GTATTATGTA | AATCAGTGGA | TATATTAAAT | GATGGCAATA | A-3' |

In Table 3 is the exon and flanking intron sequences for Exon d of Table 1 [or, the exon located on a 4.1 Kb Hind III fragment]. The exon is from 295 to 442. The primer sequences used to amplify this sequence are 269 to 293 and 512 to 536.

TABLE 3

| 5' 10 | 20 | 30 | 40 | 50 |
|---|---|---|---|---|
| TGTCCAAAAT | AGTTGACTTT | CTTTCTTTAA | TCAATAAATA | TATTACTTTA |
| 60 | 70 | 80 | 90 | 100 |
| AAGGGAAAAA | TTGCAACCTT | CCATTTAAAA | TCAGCTTTAT | ATTGAGTATT |
| 110 | 120 | 130 | 140 | 150 |
| TTTTTAAAAT | GTTGTGTGTA | CATGCTAGGT | GTGTATATTA | ATTTTTATTT |
| 160 | 170 | 180 | 190 | 200 |
| GTTACTTGAA | ACTAAACTCT | GCAAATGCAG | GAAACTATCA | GAGTGATATC |
| 210 | 220 | 230 | 240 | 250 |
| TTTGTCAGTA | TAACCAAAAA | ATATACGCTA | TATCTCTATA | ATCTGTTTTA |
| 260 | 270 | 280 | 290 | 300 |
| CATAATCCAT | CTATTTTTCT | TGATCCATAT | GCTTTTACCT | GCAGGCGATT |
| 310 | 320 | 330 | 340 | 350 |
| TGACAGATCT | GTTGAGAAAT | GGCGGCGTTT | TCATTATGAT | ATAAAGATAT |
| 360 | 370 | 380 | 390 | 400 |

TABLE 3-continued

| | | | | |
|---|---|---|---|---|
| TTAATCAGTG | GCTAACAGAA | GCTGAACAGT | TTCTCAGAAA | GACACAAATT |
| 410 | 420 | 430 | 440 | 450 |
| CCTGAGAATT | GGGAACATGC | TAAATACAAA | TGGTATCTTA | AGGTAAGTCT |
| 460 | 470 | 480 | 490 | 500 |
| TTGATTTGTT | TTTTCGAAAT | TGTATTTATC | TTCAGCACAT | CTGGACTCTT |
| 510 | 520 | 530 | 540 | 550 |
| TAACTTCTTA | AAGATCAGGT | TCTGAAGGGT | GATGGAAATT | ACTTTTGACT |
| 560 | 570 | 580 | | |
| GTTGTTGTCA | TCATTATATT | ACTAGAAAGA | AAA-3' | |

In Table 4 is the exon and flanking intron sequences for Exon e of Table 1 [0.5 Kb Hind III fragment exon]. The exon is from 396 to 571. The primer sequences used to amplify this sequence are 51 to 75 and 572 to 597.

TABLE 4

| 5' 10 | 20 | 30 | 40 | 50 |
|---|---|---|---|---|
| ACCCAAATAC | TTTGTTCATG | TTTAAATTTT | ACAACATTTC | ATAGACTATT |
| 60 | 70 | 80 | 90 | 100 |
| AAACATGGAA | CATCCTTGTG | GGGACAAGAA | ATCGAATTTG | CTCTTGAAAA |
| 110 | 120 | 130 | 140 | 150 |
| GGTTTCCAAC | TAATTGATTT | GTAGGACATT | ATAACATCCT | CTAGCTGACA |
| 160 | 170 | 180 | 190 | 200 |
| AGCTTACAAA | AATAAAAACT | GGAGCTAACC | GAGAGGGTGC | TTTTTTCCCT |
| 210 | 220 | 230 | 240 | 250 |
| GACACATAAA | AGGTGTCTTT | CTGTCTTGTA | TCCTTTGGAT | ATGGGCATGT |
| 260 | 270 | 280 | 290 | 300 |
| CAGTTTCATA | GGGAAATTTT | CACATGGAGC | TTTTGTATTT | CTTTCTTTGC |
| 310 | 320 | 330 | 340 | 350 |
| CAGTACAACT | GCATGTGGTA | GCACACTGTT | TAATCTTTTC | TCAAATAAAA |
| 360 | 370 | 380 | 390 | 400 |
| AGACATGGGG | CTTCATTTTT | GTTTTGCCTT | TTTGGTATCT | TACAGGAACT |
| 410 | 420 | 430 | 440 | 450 |
| CCAGGATGGC | ATTGGGCAGC | GGCAAACTGT | TGTCAGAACA | TTGAATGCAA |
| 460 | 470 | 480 | 490 | 500 |
| CTGGGGAAGA | AATAATTCAG | CAATCCTCAA | AAACAGATGC | CAGTATTCTA |
| 510 | 520 | 530 | 540 | 550 |
| CAGGAAAAAT | TGGGAAGCCT | GAATCTGCGG | TGGCAGGAGG | TCTGCAAACA |
| 560 | 570 | 580 | 590 | 600 |
| GCTGTCAGAC | AGAAAAAAGA | GGTAGGGCGA | CAGATCTAAT | AGGAATGAAA |
| 610 | 620 | | | |
| ACATTTTAGC | AGACTTTTA | AGCTT-3' | | |

In Table 5 is the exon and flanking intron sequences for Exon f, Table 1 [overlaps the 1.2 Kb and 3.8 Kb Hind III fragments]. The exon is from 221 to 406. The primer sequences used to amplify this sequence are 26 to 53 and 516 to 541.

TABLE 5

| 5' 10 | 20 | 30 | 40 | 50 |
|---|---|---|---|---|
| TTTTGTAGAC | GGTTAATGAA | TAATTTTGAA | TACATTGGTT | AAATCCCAAC |
| 60 | 70 | 80 | 90 | 100 |
| ATGTAATATA | TGTAAATAAT | CAATATTATG | CTGCTAAAAT | AACACAAATC |
| 110 | 120 | 130 | 140 | 150 |
| AGTAAGATTC | TGTAATATTT | CATGATAAAT | AACTTTTGAA | AATATATTTT |
| 160 | 170 | 180 | 190 | 200 |
| TAAACATTTT | GCTTATGCCT | TGAGAATTAT | TTACCTTTTT | AAAATGTATT |
| 210 | 220 | 230 | 240 | 250 |
| TTCCTTTCAG | GTTTCCAGAG | CTTTACCTGA | GAAACAAGGA | GAAATTGAAG |
| 260 | 270 | 280 | 290 | 300 |
| CTCAAATAAA | AGACCTTGGG | CAGCTTGAAA | AAAAGCTTGA | AGACCTTGAA |
| 310 | 320 | 330 | 340 | 350 |
| GAGCAGTTAA | ATCATCTGCT | GCTGTGGTTA | TCTCCTATTA | GGAATCAGTT |
| 360 | 370 | 380 | 390 | 400 |
| GGAAATTTAT | AACCAACCAA | ACCAAGAAGG | ACCATTTGAC | GTTAAGGTAG |
| 410 | 420 | 430 | 440 | 450 |
| GGGAACTTTT | TGCTTTAATA | TTTTTGTCTT | TTTTAAGAAA | AATGGCAATA |
| 460 | 470 | 480 | 490 | 500 |
| TCACTGAATT | TTCTCATTTG | GTATCATTAT | TAAAGACAAA | ATATTACTTG |
| 510 | 520 | 530 | 540 | 550 |

TABLE 5-continued

| TTAAAGTGTG | GTAAGGAAGA | CTTTATTCAG | GATAACCACA | ATAGGCACAG |
|---|---|---|---|---|
| 560 | 570 | 580 | 590 | 600 |
| GGACCACTGC | AATGGAGTAT | TACAGGAGGT | TGGATAGAGA | GAGATTGGGC |
| 610 | 620 | 630 | 640 | 650 |
| TCAACTCTAA | ATACAGCACA | GTGGAAGTAG | GAATTTATAG | C-3' |

In Table 6 is the exon and flanking intron sequences for Exon 12. The exon is from 180 to 329. The primer sequences used to amplify this sequence are 27 to 52 and 332 to 357.

TABLE 6

| 5' 10 | 20 | 30 | 40 | 50 |
|---|---|---|---|---|
| TGAGAAATAA | TAGTTCCGGG | GTGACTGATA | GTGGGCTTTA | CTTACATCCT |
| 60 | 70 | 80 | 90 | 100 |
| TCTCAATGTC | CAATAGATGC | CCCCAAATGC | GAACATTCCA | TATATTATAA |
| 110 | 120 | 130 | 140 | 150 |
| ATTCTATTGT | TTTACATTGT | GATGTTCAGT | AATAAGTTGC | TTTCAAAGAG |
| 160 | 170 | 180 | 190 | 200 |
| GTCATAATAG | GCTTCTTTCA | AATTTTCAGT | TTACATAGAG | TTTTAATGGA |
| 210 | 220 | 230 | 240 | 250 |
| TCTCCAGAAT | CAGAAACTGA | AAGAGTTGAA | TGACTGGCTA | ACAAAACAGA |
| 260 | 270 | 280 | 290 | 300 |
| AGAAAGAACA | AGGAAAATGG | AGGAAGAGCC | TCTTGGACCT | GATCTTGAAG |
| 310 | 320 | 330 | 340 | 350 |
| ACCTAAAACG | CCAAGTACAA | CAACATAAGG | TAGGTGTATC | TTATGTTGCG |
| 360 | 370 | 380 | 390 | 400 |
| TGCTTTCTAC | TAGAAAGCAA | ACTCTGTGTA | TAGTACCTAT | ACACAGTAAC |
| 410 | 420 | 430 | 440 | 450 |
| ACAGATGACA | TGGTTGATGG | GAGAGAATTA | AAACTTAAAG | TCAGCCATAT |
| 460 | 470 | 480 | 490 | 500 |
| TTTAAAAATT | ATTTTTACCT | AATTGTTTTT | GCAATCTTTG | TTGCCAATGG |
| 510 | 520 | 530 | 540 | 550 |
| CCTTGAATAA | GTCCCCTCCA | AAATTCAGGT | GATTGTATTA | GGAGATGGAA |
| 560 | 570 | 580 | 590 | 600 |
| TATTTAAGGG | TGAATAATCC | ATCAGGGCTC | CTCCCTTAAG | AATAGGATCA |
| 610 | 620 | 630 | 640 | 650 |
| AGTCCCATAT | AAAAGAGGCT | TCACACAGTG | TTCTCCTATC | TCTTGACCCT |
| 660 | 670 | 680 | 690 | 700 |
| CCACCATGCA | CCACCATGTG | AAAACTCTGT | GAAAAGGCCC | TCACCAGATG |
| 710 | 720 | 730 | 740 | 750 |
| CTAACATCTT | GATCTTGGAT | TTCCCAAACT | CGAGAACTGT | GAAAAAATAA |
| 760 | 770 | 780 | 790 | 800 |
| AGGTACATTC | TTCCTAAATT | ACCTCATTCT | CATTTAAACA | CACAAAGTGC |
| 810 | | | | |
| ACACATAGCT | G-3' | | | |

In Table 7 is the exon and flanking intron sequences for the Exon located on a 10 Kb Hind III fragment. The exon is from 1 to 150.

TABLE 7

| 5' 10 | 20 | 30 | 40 | 50 |
|---|---|---|---|---|
| TTACTGGTGG | AAGAGTTGCC | CCTGCGCCAG | GGAATTCTCA | AACAATTAAA |
| 60 | 70 | 80 | 90 | 100 |
| TGAAACTGGA | GGACCCGTGC | TTGTAAGTGC | TCCCATAAGC | CCAGAAGAGC |
| 110 | 120 | 130 | 140 | 150 |
| AAGATAAACT | TGAAAATAAG | CTCAAGCAGA | CAAATCTCCA | GTGGATAAAG |
| 160 | 170 | 180 | 190 | 200 |
| GTTAGACATT | AACCATCTCT | TCCGTCACAT | GTGTTAAATG | TTGCAAGTAT |
| 210 | 220 | 230 | 240 | 250 |
| TTGTATGTAT | TTTGTTTCCT | GGGTGCTTCA | TTGGTCGGGG | AGGAGGCTGG |
| 260 | 270 | 280 | | |
| TATGTGGATT | GTTGTTTTGT | TTTGTTTTTT-3' | | |

In Table 8 is the exon and flanking intron sequences for the Exon located on a 1.6 Kb Hind III fragment from 512 to 622.

TABLE 8

| 5' | 10 | 20 | 30 | 40 | 50 |
|---|---|---|---|---|---|
| | AAGCTTTGAT | ACTGTGCTTT | AAGTGTTTAC | CCTTTGGAAA | GAAAATAATT |
| | 60 | 70 | 80 | 90 | 100 |
| | TTGACAGTGA | TGTAGAAATA | ATTATTTGAT | ATTTATTTCA | AAACAAAATT |
| | 110 | 120 | 130 | 140 | 150 |
| | TATATCCAAT | ACTAAACACA | GAATTTGTA | AAACAATAAG | TGTATAAAGT |
| | 160 | 170 | 180 | 190 | 200 |
| | AAAATGAACA | TTAGGATTAT | TGAGATTATT | GTAGCTAAAA | CTAGTGTTTA |
| | 210 | 220 | 230 | 240 | 250 |
| | TTCATATAAA | TTATGTTAAT | AAATTGTATT | GTCATTATTG | CATTTTACTT |
| | 260 | 270 | 280 | 290 | 300 |
| | TTTTGAAAAG | TAGTTAATGC | CTGTGTTTCT | ATATGAGTAT | TATATAATTC |
| | 310 | 320 | 330 | 340 | 350 |
| | AAGAAGATAT | TGGATGAATT | TTTTTTTTAA | GTTTAATGTG | TTTCACATCT |
| | 360 | 370 | 380 | 390 | 400 |
| | CTGTTTCTTT | TCTCTGCACC | AAAAGTCACA | TTTTTGTGCC | CTTATGTACC |
| | 410 | 420 | 430 | 440 | 450 |
| | AGGCAGAAAT | TGATCTGCAA | TACATGTGGA | GTCTCCAAGG | GTATATTTAA |
| | 460 | 470 | 480 | 490 | 500 |
| | ATTTAGTAAT | TTTATTGCTA | ACTGTGAAGT | TAATCTGCAC | TATATGGGTT |
| | 510 | 520 | 530 | 540 | 550 |
| | CTTTTCCCCA | GGAAACTGAA | ATAGCAGTTC | AAGCTAAACA | ACCGGATGTG |
| | 560 | 570 | 580 | 590 | 600 |
| | GAAGAGATTT | TGTCTAAAGG | GCAGCATTTG | TACAAGGAAA | AACCAGCCAC |
| | 610 | 620 | 630 | 640 | 650 |
| | TCAGCCAGTG | AAGGTAATGA | AGCAACCTCT | AGCAATATCC | ATTACCTCAT |
| | 660 | 670 | 680 | 690 | 700 |
| | AATGGGTTAT | GCTTCGCCTG | TTGTACATTT | GCCATTGACG | TGGACTATTT |
| | 710 | 720 | 730 | 740 | 750 |
| | ATAATCAGTG | AAATAACTTG | TAAGGAAATA | CTGGCCATAC | TGTAATAGCA |
| | 760 | 770 | 780 | 790 | 800 |
| | GAGGCAAAGC | TGTCTTTTTG | ATCAGCATAT | CCTATTTATA | TATTGTGATC |
| | 810 | 820 | 830 | 840 | |
| | TTAAGGCTAT | TAACGAGTCA | TTGCTTTAAA | GGACTCATTT | CTGTC-3' |

In Table 9 is the exon and flanking intron sequences for the Exon located on a 3.1 Kb Hind III fragment, The exon is from 519 to 751.

TABLE 9

| 5' | 103 | 113 | 123 | 133 | 143 |
|---|---|---|---|---|---|
| | CCCATCTTGT | TTTGCCTTTG | TTTTTTCTTG | AATAAAAAAA | AAATAAGTAA |
| | 153 | 163 | 173 | 183 | 193 |
| | AATTTATTTC | CCTGGCAAGG | TCTGAAAACT | TTTGTTTTCT | TTACCACTTC |
| | 203 | 213 | 223 | 233 | 243 |
| | CACAATGTAT | ATGATTGTTA | CTGAGAAGGC | TTATTTAACT | TAAGTTACTT |
| | 253 | 263 | 273 | 283 | 293 |
| | GTCCAGGCAT | GAGAATGAGC | AAAATCGTTT | TTTAAAAAAT | TGTTAAATGT |
| | 303 | 313 | 323 | 333 | 343 |
| | ATATTAATGA | AAAGGTTGAA | TCTTTTCATT | TTCTACCATG | TATTGCTAAA |
| | 353 | 363 | 373 | 383 | 393 |
| | CAAAGTATCC | ACATTGTTAG | AAAAAGATAT | ATAATGTCAT | GAATAAGAGT |
| | 403 | 413 | 423 | 433 | 443 |
| | TTGGCTCAAA | TTGTTACTCT | TCAATTAAAT | TTGACTTATT | GTTATTGAAA |
| | 453 | 463 | 473 | 483 | 493 |
| | TTGGCTCTTT | AGCTTGTGTT | TCTAATTTTT | CTTTTTCTTC | TTTTTTCCTT |
| | 503 | 513 | 523 | 533 | 543 |
| | TTTGCAAAAA | CCCAAAATAT | TTTAGCTCCT | ACTCAGACTG | TTACTCTGGT |
| | 553 | 563 | 573 | 583 | 593 |
| | GACACAACCT | GTGGTTACTA | AGGAAACTGC | CATCTCCAAA | CTAGAAATGC |
| | 603 | 613 | 623 | 633 | 643 |
| | CATCTTCCTT | GATGTTGGAG | GTACCTGCTC | TGGCAGATTT | CAACCGGGCT |
| | 653 | 663 | 673 | 683 | 693 |
| | TGGACAGAAC | TTACCGACTG | GCTTTCTCTG | CTTGATCAAG | TTATAAAATC |
| | 703 | 713 | 723 | 733 | 743 |
| | ACAGAGGGTG | ATGGTGGGTG | ACCTTGAGGA | TATCAACGAG | ATGATCATCA |
| | 753 | 763 | 773 | 783 | 793 |
| | AGCAGAAGGT | ATGAGAAAAA | ATGATAAAAG | TTGGCAGAAG | TTTTTCTTTA |
| | 803 | 813 | 823 | 833 | 843 |
| | AAATGAAGAT | TTTCCACCAA | TCACTTTACT | CTCCTAGACC | ATTTCCCACC |
| | 853 | 863 | 873 | 883 | 893 |
| | AGTTCTTAGG | CAACTGTTTC | TCTCTCAGCA | AACACATTAC | TCTCACTATT |

TABLE 9-continued

| 903 | 913 | 923 | 933 | 943 |
|---|---|---|---|---|
| CAGCCTAAGT | ATAATCAGGT | ATAAATTAAT | GCAAATAACA | AAAGTAGCCA |
| 953 | 963 | 973 | 983 | 993 |
| TACATTAAAA | AGGAAAATAT | ACAAAAAAAA | AAAAAAAAAA | AAGCCAGAAA |
| 1003 | 1013 | | | |
| CCTACAGAAT | AGTGCTCTAG | TAATTAC-3' | | |

In Table 10 is the exon and flanking intron sequences for the Exon located on a 1.5 Kb Hind III fragment. The exon is from 190 to 337.

TABLE 10

| 5' 10 | 20 | 30 | 40 | 50 |
|---|---|---|---|---|
| ATCTCTATCA | TTAGAGATCT | GAATATGAAA | TACTTGTCAA | AGTGAATGAA |
| 60 | 70 | 80 | 90 | 100 |
| AATTTNNTAA | ATTATGTATG | GTTAACATCT | TTAAATTGCT | TATTTTTAAA |
| 110 | 120 | 130 | 140 | 150 |
| TTGCCATGTT | TGTGTCCCAG | TTTGCATTAA | CAAATAGTTT | GAGAACTATG |
| 160 | 170 | 180 | 190 | 200 |
| TTGGAAAAAA | AAATAACAAT | TTTATTCTTC | TTTCTCCAGG | CTAGAAGAAC |
| 210 | 220 | 230 | 240 | 250 |
| AAAAGAATAT | CTTGTCAGAA | TTTCAAAGAG | ATTTAAATGA | ATTTGTTTTA |
| 260 | 270 | 280 | 290 | 300 |
| TGGTTGGAGG | AAGCAGATAA | CATTGCTAGT | ATCCCACTTG | AACCTGGAAA |
| 310 | 320 | 330 | 340 | 350 |
| AGAGCAGCAA | CTAAAAGAAA | AGCTTGAGCA | AGTCAAGGTA | ATTTTATTTT |
| 360 | 370 | 380 | 390 | 400 |
| CTCAAATCCC | CCAGGGCCTG | CTTGCATAAA | GAAGTATATG | AATCTATTTT |
| 410 | 420 | 430 | 440 | 450 |
| TTAATTCAAT | CATTGGTTTT | CTGCCCATTA | GGTTATTCAT | AGTTCCTTGC |
| 460 | 470 | 480 | 490 | 500 |
| TAAAGTGTTT | TTCTCACAAC | TTTATTTCTT | CTTAACCCTG | CAGTTCTGAA |
| 510 | 520 | 530 | 540 | 550 |
| CCAGTGCACA | TAAGAACATA | TGTATATATG | TGTGTGTGTG | TATTTATATA |
| 560 | 570 | 580 | 590 | 600 |
| TACACACACA | CATATTGCAT | CTATACATCT | ACACATATAG | ATGTATAGAT |
| 610 | 620 | 630 | 640 | 650 |
| TCAATATGTC | TAAAAATGTA | TATAATTCAC | AGTTTTTATC | TTTGATTTGA |
| 660 | 670 | 680 | | |
| ATATTTAAGG | GACTGAGACT | CACACTCATA | TACTTTT-3' | |

EXAMPLE 3

Prenatal Diagnosis and Detection of DMD Using PCR

An example of prenatal diagnosis with PCR deletion detection is demonstrated using synthesized oligonucleotide primers (set b, Table 1). This primer set corresponds to the intron sequences flanking Exon 17 of the human DMD gene, a region which has been isolated and sequenced (Table 2).

Figure 2:
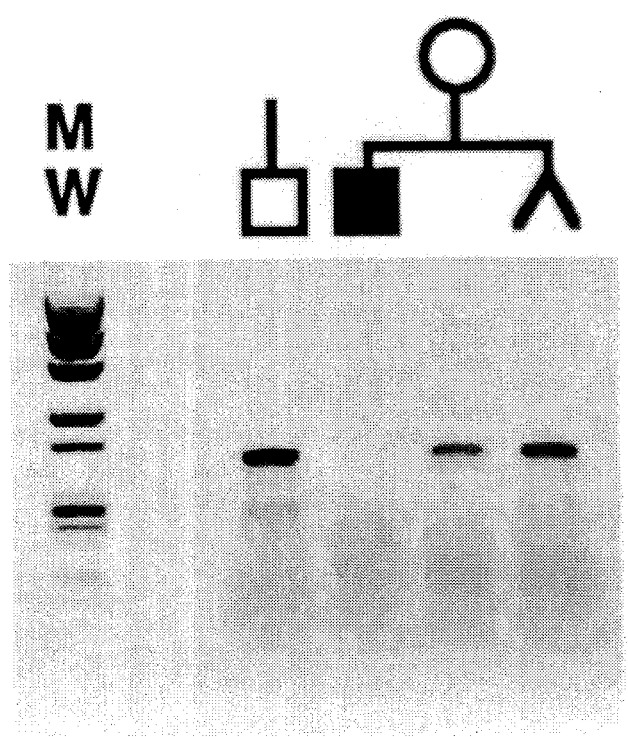
FIG. 2 is an example of a PCR reaction used to detect a deletion in fetal DNA for prenatal diagnosis.

The results of this analysis are shown in FIG. 2. The PCR products (one-twentieth of the total reaction) were obtained with template DNA isolated from a control male □, the male fetus being diagnosed Λ, the DMD carrier mother (O) and an affected male brother of the fetus ■. Also shown is a DNA molecular weight standard (MW; Hae III digested φX174 DNA). The results demonstrate that the affected male carries a deletion of Exon 17, which was not amplified, but that the fetus does not carry the deletion and is therefore unaffected. These results indicate that PCR is useful in the diagnosis of DMD cases containing a deletion involving this exon.

EXAMPLE 4

Multiplex Detection

Figure 3A:
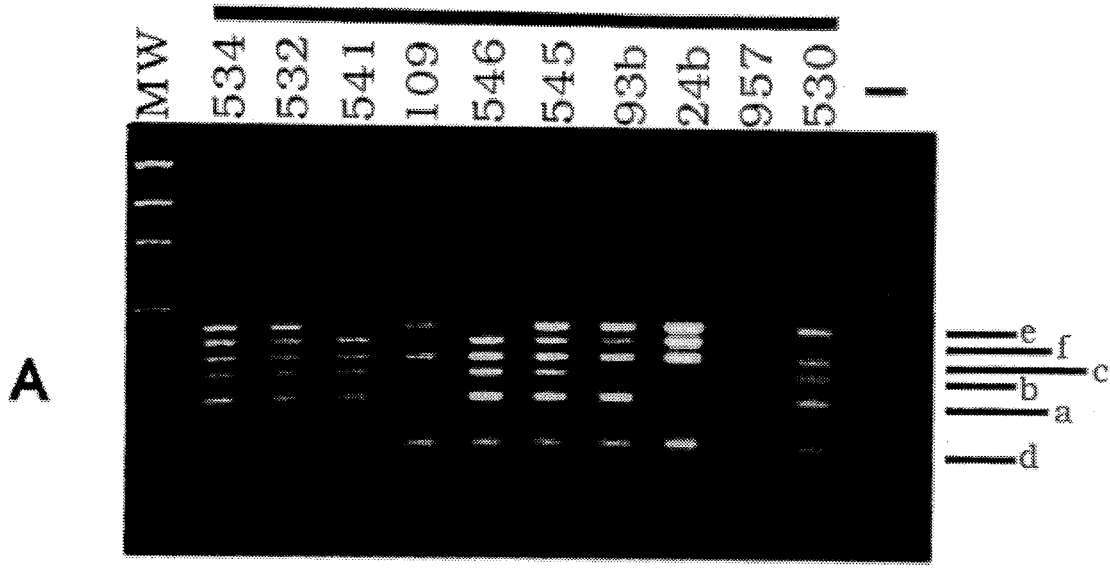
FIG. 3A and 3B represents the multiplex DNA amplification of lymphoblast DNA from unrelated male DMD patients. 3A. and 3B. show two sets of ten samples. Each DRL # refers to the R. J. Kleberg Center for Human Genetics Diagnostic Research Laboratory family number. MW: Hae III digested φX174 DNA. (–): no template DNA added to the reaction. The relationship between the amplified region and the region on the gene is indicated to the right of A. The letters correspond to those on FIG. 1.
Figure 3B:

An example of multiplex detection is shown in FIGS. 3A and 3B.

This analysis was done using six primer pairs (sets a–f, Table 1) and the conditions described in Example 1. Automatic rather than manual amplification was performed.

These oligonucleotide primers represent the flanking regions of six separate DMD gene exons. They were combined into a reaction vial and used for multiplex genomic DNA amplifications. Template DNA was isolated from lymphoblasts (from blood sample). Analysis was by agarose gel electrophoresis.

When non-deleted DNA was used as a template, the six dispersed regions of the DMD gene were simultaneously and specificially amplified (FIG. 3A, Sample #534). Discrete deletions, which were detected with this method, are shown in FIGS. 3A and 3B. Several DNA samples containing normal, partial or total DMD gene deletions are shown. FIGS. 3A and 3B also show a DNA molecular weight standard (MW: Hae III digested φX174 DNA), and a negative control (−) where no template DNA was added to the reactions. FIG. 3A also indicates which amplified DNA fragment corresponds to which exon (a–f) of FIG. 1.

EXAMPLE 5

Prenatal Diagnosis

Figure 4:
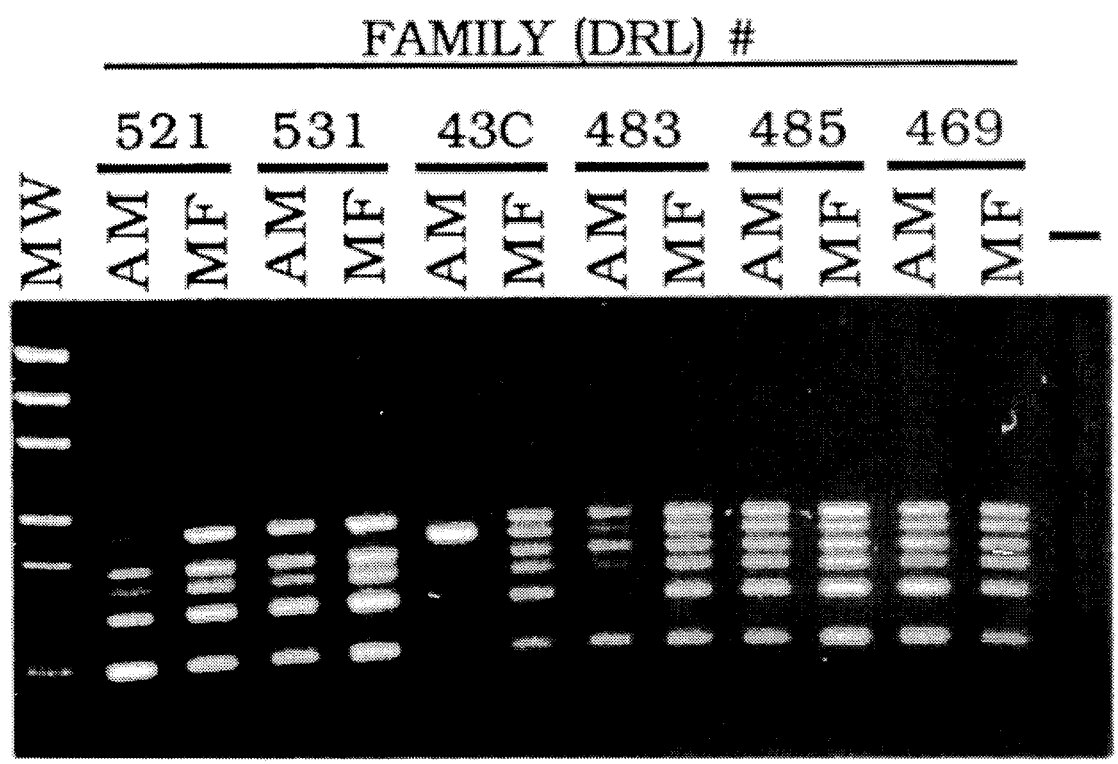
FIG. 4 represents Multiplex DNA amplification for prenatal diagnosis of DMD. Shown are the results of amplification using DNA from an affected male (AM; lymphoblast DNA) and a male fetus (MF; cultured amniotic fluid cell DNA) from six different families. Both the affected male and the fetal DNAs of DRL #s 521 and 531 display a deletion of region f (FIG. 1); diagnosing these fetuses as affected. In DRL #43C the affected male is deleted for all regions except f, while the fetus is unaffected. The affected male in DRL #483 is deleted for region a, while the male fetus is unaffected. Neither of the samples from DRL #s 485 or 469 displayed a deletion with this technique.

Multiplex PCR has been used successfully in several prenatal diagnoses. The conditions are as described above in Example 1. FIG. 4 shows Multiplex DNA amplification for prenatal diagnosis of DMD. Shown are the results of amplification using DNA from affected males (AM; lymphoblast DNA) and male fetuses (MF; cultured amniotic fluid cell DNA) from six different families. Analysis was as described in Example 1. Both the affected male and the fetal DNA of DRL #s 521 and 531 display a deletion of region f (FIG. 1). Thus these fetuses were diagnosed as affected. In DRL #43C the affected male is deleted for all regions except f, while the fetus is unaffected. The affected male in DRL #483 is deleted for region a, while the male fetus is unaffected. Neither of the samples from DRL #s 485 or 469 displayed a deletion with this technique. Thus, if a deletion defect causes DMD in these families it occurred in an untested exon.

EXAMPLE 6

Figure 5:
FIG. 5 represents Multiplex DNA amplification from chorionic villus specimen (CVS) DNA. Both the affected male (AM; lymphoblast DNA) and the male fetus (MF; CVS DNA) from DRL #92 display a deletion of regions e and f (FIG. 1), diagnosing the fetus as affected. CVS DNA from DRL #120 did not display a deletion with this technique.

Prenatal Diagnosis Using Multiplex DNA Amplification of Chorionic Villus Specimen (CVS) DNA FIG. 5 demonstrates Multiplex DNA amplification from CVS DNA. Both the affected male (AM; lymphoblast DNA) and the male fetus (MF; CVS DNA) from DRL #92 display a deletion of regions e and f (FIG. 1). Thus the fetus was diagnosed as affected. CVS DNA from DRL #120 did not display a deletion with this technique. Samples were analyzed as described in Example 1. These results demonstrate that the multiplex amplification technique works well for prenatal diagnosis when CVS DNA is used as the template for amplification.

EXAMPLE 7

Multiplex Amplification of Seven Separate Exons of the DMD Gene

Figure 6:
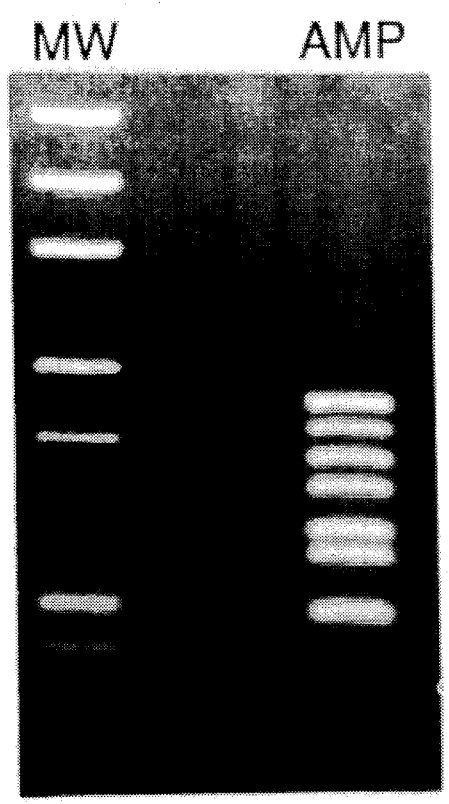
FIG. 6 shows amplification of seven exon regions of the DMD locus.

This example demonstrates that seven separate DNA sequences can be simultaneously amplified using the multiplex amplification technique. Conditions were as described in Example 1. Primer sets a–g (Table 1) were added to the reaction. Thus seven exon regions of the DMD gene (FIG. 1) were amplified (FIG. 6).

EXAMPLE 8

Multiplex DNA Amplification for the Simultaneous Detection of Mutations Leading to Multiple Common Genetic Diseases This example describes how the multiplex amplification technique can be used to simultaneously screen a newborn male for any of the most common mutations leading to DMD, sickle-cell anemia and $\alpha_1$-antitrypsin deficiency. In this assay any or all of the primers sets listed in Table 1 can be used for multiplex DNA amplification to diagnose the majority of possible DMD gene deletions. Additionally, primer sets can be added to the amplification reaction to identify mutations leading to additional genetic diseases. Other primer sets include:

A.    5'-TGGTCTCCTTAAACCTGTCTT-3'5'-ACACAACTGTGTTCACTAG-3'

These oligonucleotides amplify a 167 bp segment of the human β-globin gene, containing the DNA base that is mutated in $\beta^s$ (sickle-cell) hemoglobinopathy. The presence or absence of the mutant $\beta^s$ sequence is then determined either by separate dot blot or Southern blot hybridization of the multiplex amplification reaction with each of two labelled allele-specific oligonucleotide (ASO) probes specific for the normal or $\beta^s$ sequence. The sequence of these two ASO probes is:

1) Normal: 5'-CTCCTGAGGAGA-3'

2) $\beta^s$: 5'-CTCCTGTGGAGA-3'

If dot blot hybridization is used, a separate application of DNA from the multiplex amplification reaction to a DNA membrane, such as nitrocellulose, is required for each probe that will be used in the hybridization. Hybridization of each labelled probe, whether the probes are complementary to individual alleles of a given gene or to separate genes, must be performed individually. Alternatively and preferably, two aliquots of the amplification reaction are separately electrophoresed on agarose gels and transferred to nitrocellulose or a similar membrane using Southern analysis. Each of the two Southern blots are then hybridized with one member of each labelled set of specific ASO primers. Thus each known mutant or normal allele of each DNA fragment amplified in the multiplex reaction can be determined.

In addition to the above described primer sets the following oligonucleotide primers can also be added to the amplification procedure:

B.    5'-ACGTGGAGTGACGATGCTCTTCCC-3'5'-GTGGGATTCACCACTTTTCCC-3'

These primers produce a 450 bp DNA fragment containing the DNA base change that produces the Z allele of the $\alpha_1$-antitrypsin gene and leads to $\alpha_1$-antitrypsin deficiency. The Z allele and the normal M allele are distinguished from other alleles in the multiplex amplification reaction by hybridization with the ASO probes:

1) Normal (M)allele:5'-ATCGACGAGAAA-3'

2) Mutant (Z)allele:5'-ATCGACAAGAAA-3'

Hybridization analysis is performed in parallel with the β-globin probes as described above.

In addition, the oligonucleotides

C.    5'-GAAGTCAAGGACACCGAGGAA-3'5'-AGCCCTCTGGCCAGTCCTAGTG-3' can also be added to the multiplex reaction to produce a 340 bp DNA region of the $\alpha_1$-antitrypsin gene that contains the DNA base change that produces the S allele and leads to $\alpha_1$-antitrypsin deficiency. The S allele is distinguished from other alleles in the multiplex amplification as described above for the $\beta^s$ and Z alleles by using the two ASO probes specific for the M and S allele:

Normal (M)allele 5'-ACCTGGAAAATG-3'

Mutant (S)allele 5'-ACCTGGTAAATG-3'

Using the primers described in Table 1 and in A, B and C of this example, the common mutations leading to DMD, sickle cell anemia and $\alpha_1$-antitrypsin deficiency can be simultaneously determined.

One skilled in the art will readily appreciate that the present invention is well adapted to carry out the objects and obtain the ends and advantages mentioned, as well, those inherent therein. The methods, procedures and techniques described herein are presently representative of the preferred embodiments, are intended to be exemplary, and are not intended as limitations on the scope. Changes therein and other uses will occur to those skilled in the art which are encompassed within the spirit of the invention or defined by the scope of the appended claims.

What is claimed is:

1. A method for simultaneously detecting known deletions from at least three DNA sequences, comprising the steps of:

treating said DNA to form single-stranded complementary strands;

adding at least three pairs of oligonucleotide primers, each pair specific for a different sequence, one primer of each pair substantially complementary to a part of the sequence in the sense-strand and the other primer of each pair substantially complementary to a different part of the same sequence in the complementary anti-sense strand;

annealing the at least three pairs of primers to their complementary sequences, all primers being subjected to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded molecules by repeating, at least once, said annealing, extending and separating steps; and identifying said amplified extension products from each different sequence.

2. The method of claim 1 for detecting deletions from at least genomic DNA sequences, wherein said sequences are selected from the group of known sequences on the X and Y chromosomes.

3. The method of claim 2 for the detection of X-linked disease, wherein said genomic DNA sequences contain a deletion that causes a genetic disease.

4. The method of claim 3 for the detection of said X-linked genetic diseases selected from the group consisting of ornithine transcarbamylase deficiency, hypoxanthine phosphoribosyltransferfase deficiency, steroid sulfatase deficiency and X-linked muscular dystrophy.

5. The method of claim 4 for the detection of X-linked muscular dystrophy, wherein each pair of said at least three pairs of primers are complementary to different sequences within the gene coding for the dystrophin protein.

6. The method of claim 5, wherein the at least three pairs of primers is selected from the group consisting of:

(1) 5'-GACTTTCGATGTTGAGATTACTTTCCC-3'
(2) 5'-AAGCTTGAGATGCTCTCACCTTTTCC-3',
(1) 5'-GTCCTTTACACACTTTACCTGTTGAG-3'
(2) 5'-GGCCTCATTCTCATGTTCTAATTAG-3',
(1) 5'-AAACATGGAACATCCTTGTGGGGAC-3'
(2) 5'-CATTCCTATTAGATCTGTCGCCCTAC-3',
(1) 5'-GATAGTGGGCTTTACTTACATCCTTC-3'
(2) 5'-GAAAGCACGCAACATAAGATACACCT-3',
(1) 5'-CTTGATCCATATGCTTTTACCTGCA-3'
(2) 5'-TCCATCACCCTTCAGAACCTGATCT-3',
(1) 5'-TTGAATACATTGGTTAAATCCCAACATG-3'
(2) 5'-CCTGAATAAAGTCTTCCTTACCACAC-3', and
(1) 5'-TTCTACCACATCCCATTTTCTTCCA-3'
(2) 5'-GATGGCAAAAGTGTTGAGAAAAAGTC-3'.

7. The method of claim 3, wherein said genomic DNA is from fetal tissue.

8. The method of claim 1 for detecting deletions from at least three genomic DNA sequences, wherein the at least three pairs of primers is selected from the group consisting of:

(1) 5'-GACTTTCGATGTTGAGATTACTTTCCC-3'
(2) 5'-AAGCTTGAGATGCTCTCACCTTTTCC-3',
(1) 5'-GTCCTTTACACACTTTACCTGTTGAG-3'
(2) 5'-GGCCTCATTCTCATGTTCTAATTAG-3',
(1) 5'-AAACATGGAACATCCTTGTGGGGAC-3'
(2) 5'-CATTCCTATTAGATCTGTCGCCCTAC-3',
(1) 5'-GATAGTGGGCTTTACTTACATCCTTC-3',
(2) 5'-GAAAGCACGCAACATAAGATACACCT-3',
(1) 5'-CTTGATCCATATGCTTTTACCTGCA-3'
(2) 5'-TCCATCACCCTTCAGAACCTGATCT-3',
(1) 5'-TTGAATACATTGGTTAAATCCCAACATG-3'
(2) 5'-CCTGAATAAAGTCTTCCTTACCACAC-3',
(1) 5'-TTCTACCACATCCCATTTTCTTCCA-3'
(2) 5'-GATGGCAAAAGTGTTGAGAAAAAGTC-3',
(1) 5'-TGGTCTCCTTAAACCTGTCTT-3'
(2) 5'-ACACAACTGTGTTCACTAG-3',
(1) 5'-ACGTGGAGTGACGATGCTCTTCCC-3'
(2) 5'-GTGGGATTCACCACTTTTCCC-3', and
(1) 5'-GAAGTCAAGGACACCGAGGAA-3'
(2) 5'-AGCCCTCTGGCCAGTCCTAGTG-3'.

9. The method of claim 1, wherein said at least three pairs of primers have Tms such that the lowest Tm and the highest Tm vary by no more than 8.3° C.

10. The method of claim 1, wherein said at least three pairs of primers have Tms such that the lower Tm of each pair varies from the lower Tm of each other pair by no more than 4.4° C.

11. A method for simultaneously detecting at least three DNA sequences, comprising the steps of:

adding to a common reaction vessel containing a sample mixture of at least three distinct, target sequences in single-stranded form, at least three pairs of oligonucleotide primers, each pair specific for a different sequence, one primer of each pair substantially complementary to a part of the sequence in the sense-strand and the other primer of each pair substantially complementary to a different part of the same sequence in the complementary anti-sense strand;

annealing the at least three pairs of primers to their complementary sequences, all primers being subject to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded target sequences by repeating, at least once, said annealing, extending and separating steps; and identifying whether amplified extension products have been synthesized from each different sequence, as a result of the presence or absence of each target sequence.

12. A method for simultaneously detecting known deletions from at least three DNA sequences, comprising the steps of:

treating said DNA to form single-stranded complementary strands;

adding at least three pairs of oligonucleotide primers, each pair specific for a different sequence, one primer of each pair substantially complementary to a part of the sequence in the sense-strand and the other primer of each pair substantially complementary to a different part of the same sequence in the complementary antisense strand and each primer having a Tm such that the lowest Tm and highest Tm of all added primers varies by no more than 8.3° C.;

annealing the at least three pairs of primers to their complementary sequences, all primers being subjected to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded molecules by repeating, at least once, said annealing, extending and separating steps; and identifying said amplified extension products from each different sequence; and analyzing said amplified extension products to detect known deletions.

13. A method for simultaneously detecting a presence or absence of at least three target DNA sequences, comprising the steps of:

adding to a common reaction vessel containing a sample mixture of at least three distinct, target sequences in single-stranded form, at least three pairs of oligonucleotide primers, each pair specific for a different sequence, one primer of each pair substantially complementary to a part of the sequence in the sense-strand and the other primer of each pair substantially complementary to a different part of the same sequence in the complementary anti-sense strand and each primer having a Tm such that the lowest Tm and highest Tm of all added primers varies by no more than 8.3° C.;

annealing the at least three pairs of primers to their complementary sequences, all primers being subject to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded target sequences by repeating, at least once, said annealing, extending and separating steps; and identifying whether amplified extension products have been synthesized from each different target sequence, wherein a presence of an extension product indicates the presence of a target sequence and an absence of an extension product indicates the absence of a target sequence.

14. A method for simultaneously detecting known deletions from at least three DNA sequences, comprising the steps of:

treating said DNA to form single-stranded complementary strands;

adding at least three pairs of oligonucleotide primers, each pair specific for a different sequence, one primer of each pair substantially complementary to a part of the sequence in the sense-strand and the other primer of each pair substantially complementary to a different part of the same sequence in the complementary anti-sense strand and each primer having a Tm such that the lowest Tm and highest Tm of all added primers varies by no more than 4.4° C.;

annealing the at least three pairs of primers to their complementary sequences, all primers being subjected to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded molecules by repeating, at least once, said annealing, extending and separating steps; and identifying said amplified extension products from each different sequence; and analyzing said amplified extension products to detect known deletions.

15. A method for simultaneously detecting at least three target DNA sequences, comprising the steps of:

adding to a common reaction vessel containing a sample mixture of at least three distinct, target sequences in single-stranded form, at least three pairs of oligonucleotide primers, each pair specific for a different sequence, one primer of each pair substantially complementary to a part of the sequence in the sense-strand and the other primer of each pair substantially complementary to a different part of the same sequence in the complementary anti-sense strand and each primer having a Tm such that the lowest Tm and highest Tm of all added primers varies by no more than 4.4° C.;

annealing the at least three pairs of primers to their complementary sequences, all primers being subject to the same reaction conditions;

simultaneously extending said at least three pairs of annealed primers from each primer's 3' terminus to synthesize an extension product complementary to the strands annealed to each primer, said extension products, after separation from their complement, being capable of serving as templates for the synthesis of an extension product from the other primer of each pair;

separating said extension products from said templates to produce single-stranded molecules;

amplifying said single stranded target sequences by repeating, at least once, said annealing, extending and separating steps; and identifying whether amplified extension products have been synthesized from each different target sequence, wherein a presence of an extension product indicates the presence of a target sequence and an absence of an extension product indicates the absence of a target sequence.

* * * * *

UNITED STATES PATENT AND TRADEMARK OFFICE
CERTIFICATE OF CORRECTION

PATENT NO.    : 5,582,989
DATED         : December 10, 1996
INVENTOR(S)   : C. T. Caskey It is certified that error appears in the above-identified patent and that said Letters Patent is hereby corrected as shown below:

Column 1,
Line 4, insert:
-- This invention was made with government support under Grant No. R22 DK35369 awarded by the National Institutes of Health. The United States Government may have certain rights in the invention. --

Signed and Sealed this

Thirtieth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,582,989
DATED : December 10, 1996
INVENTOR(S) : C. T. Caskey

It is certified that error appears in the above-identified patent and that said Letters Patent is hereby corrected as shown below:

Column 1,
Line 4, delete -- This invention was made with government support under Grant No. R22 DK35369 awarded by the National Institutes of Health. The United States Government may have certain rights in the invention. --

Signed and Sealed this

Eighteenth Day of May, 2004

JON W. DUDAS
*Acting Director of the United States Patent and Trademark Office*

EX PARTE REEXAMINATION CERTIFICATE (6681st)

United States Patent
Caskey et al.

(10) Number: US 5,582,989 C1
(45) Certificate Issued: Mar. 3, 2009

(54) MULTIPLEX GENOMIC DNA AMPLIFICATION FOR DELETION DETECTION

(75) Inventors: Charles T. Caskey, Houston, TX (US); Jeffrey S. Chamberlain, Houston, TX (US); Richard A. L. Gibbs, Houston, TX (US); Joel E. Ranier, Houston, TX (US); Phi N. Nguyen, Houston, TX (US)

(73) Assignee: Baylor College of Medicine, Houston, TX (US)

Reexamination Request:
No. 90/010,062, Dec. 4, 2007

Reexamination Certificate for:
Patent No.: 5,582,989
Issued: Dec. 10, 1996
Appl. No.: 08/315,673
Filed: Sep. 30, 1994

Related U.S. Application Data

(63) Continuation of application No. 08/060,463, filed on May 12, 1993, now abandoned, which is a continuation of application No. 07/770,742, filed on Oct. 2, 1991, now abandoned, and a continuation of application No. 07/256,689, filed on Oct. 12, 1988, now abandoned.

(51) Int. Cl.
*C12Q 1/68* (2006.01)
*C12P 19/34* (2006.01)
*C07K 14/47* (2006.01)
*C07K 14/435* (2006.01)

(52) U.S. Cl. ............ 435/6; 435/91.1; 435/91.2; 536/22.1; 536/23.1; 536/24.1; 536/24.3; 536/24.31; 536/24.32; 536/24.33

(58) Field of Classification Search .......... None
See application file for complete search history.

(56) References Cited

U.S. PATENT DOCUMENTS 4,965,190 A  10/1990  Woo et al.

FOREIGN PATENT DOCUMENTS

EP  0200362  12/1986

OTHER PUBLICATIONS

J.C. Diaz–Chico, K.G. Yang, T.A. Stoming, D.G. Efremov, A. Kutlar, F. Kutlar, M. Aksoy, C. Altay, A. Gurgey, Y. Kilinc, and T.H.J. Juisman. Mild and Severe β–Thalassemia Among Homozygotes from Turkey: Identification of the Types by Hybridizatino of Amplified DNA with Synthetic Probes. Blood, vol. 71, No. 1 (Jan.), 1988,: pp. 248–251.
Diaz—Chico et al. Biochim. Biophys. Acta 949:43–48, 1988.
Kogan et al. N. Engl. J. Med. 317:985–990, Oct. 15, 1987.
Kim and Smithies Nucl. Acids Res. 16:8887–8903, 1988.
Koenig et al. Cell 53: 218–228, Apr. 22, 1988.

*Primary Examiner*—Gary L Kunz

(57) ABSTRACT

The present invention relates to a method for detecting multiple DNA sequences simultaneously. The method involves amplification of multiple sequences simultaneously by annealing a plurality of paired oligonucleotide primers to single stranded DNA. One member of each pair is complementary to the sense strand of a sequences and the other member is complementary to a different segment of the antisense strand of the same sequence. The amplification occurs by alternately annealing and extending the primers. The invention also includes oligonucleotide primer sequences helpful in detecting genetic diseases and/or exogenous DNA sequences.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–5, 7 and 9–15 is confirmed.

Claims 6 and 8 were not reexamined.

* * * * *

(12) EX PARTE REEXAMINATION CERTIFICATE (9425th)
United States Patent
Caskey et al.

(10) Number: US 5,582,989 C2
(45) Certificate Issued: Nov. 26, 2012

(54) MULTIPLEX GENOMIC DNA AMPLIFICATION FOR DELETION DETECTION

(75) Inventors: Charles T. Caskey, Houston, TX (US); Jeffrey S. Chamberlain, Houston, TX (US); Richard A. L. Gibbs, Houston, TX (US); Joel E. Ranier, Houston, TX (US); Phi N. Nguyen, Houston, TX (US)

(73) Assignee: Baylor College of Medicine, Houston, TX (US)

Reexamination Request:
No. 90/009,495, Jun. 18, 2009

Reexamination Certificate for:
Patent No.: 5,582,989
Issued: Dec. 10, 1996
Appl. No.: 08/315,673
Filed: Sep. 30, 1994

Reexamination Certificate C1 5,582,989 issued Mar. 3, 2009

Certificate of Correction issued Dec. 30, 2003.
Certificate of Correction issued May 18, 2004.

Related U.S. Application Data

(63) Continuation of application No. 08/060,463, filed on May 12, 1993, now abandoned, which is a continuation of application No. 07/770,742, filed on Oct. 2, 1991, now abandoned, and a continuation of application No. 07/256,689, filed on Oct. 12, 1988, now abandoned.

(51) Int. Cl.
*C07K 14/47* (2006.01)
*C12Q 1/00* (2006.01)

(52) U.S. Cl. ...... 435/6.18; 435/6.1; 435/91.1; 435/91.2; 435/22.1; 435/23.1; 435/24.1; 435/24.3; 435/24.31; 435/24.32; 435/24.33

(58) Field of Classification Search .................. None
See application file for complete search history.

(56) References Cited

To view the complete listing of prior art documents cited during the proceeding for Reexamination Control Number 90/009,495, please refer to the USPTO's public Patent Application Information Retrieval (PAIR) system under the Display References tab.

*Primary Examiner* — Shri Ponnaluri

(57) ABSTRACT

The present invention relates to a method for detecting multiple DNA sequences simultaneously. The method involves amplification of multiple sequences simultaneously by annealing a plurality of paired oligonucleotide primers to single stranded DNA. One member of each pair is complementary to the sense strand of a sequences and the other member is complementary to a different segment of the antisense strand of the same sequence. The amplification occurs by alternately annealing and extending the primers. The invention also includes oligonucleotide primer sequences helpful in detecting genetic diseases and/or exogenous DNA sequences.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 12-15 is confirmed.

Claims 1-5, 7 and 11 are cancelled.

Claims 6 and 8-10 are determined to be patentable as amended.

6. [The method of claim 5] *A method for simultaneously detecting known deletions from at least three DNA sequences, comprising the steps of:*
   *treating said DNA to form single-stranded complementary strands;*
   *adding at least three pairs of oligonucleotide primers to a common reaction vessel, each pair specific for a different sequence, one primer of each pair substantially complementary to a part of the sequence in the sense-strand and the other primer of each pair substantially complementary to a different part of the same sequence in the complementary anti-sense strand;*
   *annealing the at least three pairs of primers to their complementary sequences, all primers being subjected to the same reaction conditions;*
   *simultaneously extending said at least three pairs of annealed primers from each primer's 3' terminus to synthesize an extension product complementary to the strands annealed to each primer, said extension products, after separation from their complement, serving as templates for the synthesis of an extension product from the other primer of each pair;*
   *separating said extension products from said templates to produce single-stranded molecules;*
   *amplifying said single stranded molecules by repeating, at least once, said annealing, extending and separating steps; and*
   *identifying said amplified extension products by differentiating each extension product from each different sequence in a mixture, wherein the at least three pairs of primers is selected from the group consisting of:*
   (1) 5'-GACTTTCGATGTTGAGATTACTTTCCC-3'
   (2) 5'-AAGCTTGAGATGCTCTCACCTTTTCC-3',
   (1) 5'-GTCCTTTACACACTTTACCTGTTGAG-3'
   (2) 5'-GGCCTCATTCTCATGTTCTAATTAG-3',
   (1) 5'-AAACATGGAACATCCTTGTGGGGAC-3'
   (2) 5'-CATTCCTATTAGATCTGTCGCCCTAC-3',
   (1) 5'-GATAGTGGGCTTTACTTACATCCTTC-3'
   (2) 5'-GAAAGCACGCAACATAAGATACACCT-3',
   (1) 5'-CTTGATCCATATGCTTTTACCTGCA-3'
   (2) 5'-TCCATCACCCTTCAGAACCTGATCT-3',
   (1) 5'-TTGAATACATTGGTTAAATCCCAACATG-3'
   (2) 5'-CCTGAATAAAGTCTTCCTTACCACAC-3', and
   (1) 5'-TTCTACCACATCCCATTTTCTTCCA-3'
   (2) 5'-GATGGCAAAAGTGTTGAGAAAAAGTC-3'.

8. [The method of claim 1 for detecting deletions from at least three genomic DNA sequences,] *A method for simultaneously detecting known deletions from at least three DNA sequences, comprising the steps of:*
   *treating said DNA to form single-stranded complementary strands;*
   *adding at least three pairs of oligonucleotide primers to a common reaction vessel, each pair specific for a different sequence, one primer of each pair substantially complementary to a part of the sequence in the sense-strand and the other primer of each pair substantially complementary to a different part of the same sequence in the complementary anti-sense strand;*
   *annealing the at least three pairs of primers to their complementary sequences, all primers being subjected to the same reaction conditions;*
   *simultaneously extending said at least three pairs of annealed primers from each primer's 3' terminus to synthesize an extension product complementary to the strands annealed to each primer, said extension products, after separation from their complement, serving as templates for the synthesis of an extension product from the other primer of each pair;*
   *separating said extension products from said templates to produce single-stranded molecules;*
   *amplifying said single stranded molecules by repeating, at least once, said annealing, extending and separating steps; and*
   *identifying said amplified extension products by differentiating each extension product from each different sequence in a mixture, wherein the DNA sequences are genomic sequences and* wherein the at least three pairs of primers is selected from the group consisting of:
   (1) 5'-GACTTTCGATGTTGAGATTACTTTCCC-3'
   (2) 5'-AAGCTTGAGATGCTCTCACCTTTTCC-3',
   (1) 5'-GTCCTTTACACACTTTACCTGTTGAG-3'
   (2) 5'-GGCCTCATTCTCATGTTCTAATTAG-3',
   (1) 5'-AAACATGGAACATCCTTGTGGGGAC-3'
   (2) 5'-CATTCCTATTAGATCTGTCGCCCTAC-3',
   (1) 5'-GATAGTGGGCTTTACTTACATCCTTC-3'
   (2) 5'-GAAAGCACGCAACATAAGATACACCT-3',
   (1) 5'-CTTGATCCATATGCTTTTACCTGCA-3'
   (2) 5'-TCCATCACCCTTCAGAACCTGATCT-3',
   (1) 5'-TTGAATACATTGGTTAAATCCCAACATG-3'
   (2) 5'-CCTGAATAAAGTCTTCCTTACCACAC-3',
   (1) 5'-TTCTACCACATCCCATTTTCTTCCA-3'
   (2) 5'-GATGGCAAAAGTGTTGAGAAAAAGTC-3',
   (1) 5'-TGGTCTCCTTAAACCTGTCTT-3'
   (2) 5'-ACACAACTGTGTTCACTAG-3',
   (1) 5'-ACGTGGAGTGACGATGCTCTTCCC-3'
   (2) 5'-GTGGGATTCACCACTTTTCCC-3', and
   (1) 5'-GAAGTCAAGGACACCGAGGAA-3'
   (2) 5'-AGCCCTCTGGCCAGTCCTAGTG-3'.

9. [The method of claim 1] *A method for simultaneously detecting known deletions from at least three DNA sequences, comprising the steps of:*
   *treating said DNA to form single-stranded complementary strands;*
   *adding at least three pairs of oligonucleotide primers to a common reaction vessel, each pair specific for a different sequence, one primer of each pair substantially complementary to a part of the sequence in the sense-strand and the other primer of each pair substantially complementary to a different part of the same sequence in the complementary anti-sense strand;* annealing the at least three pairs of primers to their complementary sequences, all primers being subjected to the same reaction conditions;

simultaneously extending said at least three pairs of annealed primers from each primer's 3' terminus to synthesize an extension product complementary to the strands annealed to each primer, said extension products, after separation from their complement, serving as templates for the synthesis of an extension product from the other primer of each pair;

separating said extension products from said templates to produce single-stranded molecules;

amplifying said single stranded molecules by repeating, at least once, said annealing, extending and separating steps; and identifying said amplified extension products by differentiating each extension product from each different sequence in a mixture, wherein said at least three pairs of primers have Tms such that the lowest Tm and the highest Tm vary by no more than 8.3° C.

10. [The method of claim 1] *A method for simultaneously detecting known deletions from at least three DNA sequences, comprising the steps of:*

*treating said DNA to form single-stranded complementary strands;*

*adding at least three pairs of oligonucleotide primers to a common reaction vessel, each pair specific for a different sequence, one primer of each pair substantially complementary to a part of the sequence in the sense-strand and the other primer of each pair substantially complementary to a different part of the same sequence in the complementary anti-sense strand;*

*annealing the at least three pairs of primers to their complementary sequences, all primers being subjected to the same reaction conditions;*

*simultaneously extending said at least three pairs of annealed primers from each primer's 3' terminus to synthesize an extension product complementary to the strands annealed to each primer, said extension products, after separation from their complement, serving as templates for the synthesis of an extension product from the other primer of each pair;*

*separating said extension products from said templates to produce single-stranded molecules;*

*amplifying said single stranded molecules by repeating, at least once, said annealing, extending and separating steps; and*

*identifying said amplified extension products by differentiating each extension product from each different sequence in a mixture, wherein said at least three pairs of primers have Tms such that the lower Tm of each pair varies from the lower Tm of each other pair by no more than 4.4° C.*

\* \* \* \* \*